(12) United States Patent
Afar et al.

(10) Patent No.: US 8,603,477 B2
(45) Date of Patent: Dec. 10, 2013

(54) USE OF ANTI-CS1 ANTIBODIES FOR TREATMENT OF RARE LYMPHOMAS

(75) Inventors: Daniel Afar, Short Hills, NJ (US); Eric Hsi, Orange Village, OH (US)

(73) Assignees: Abbvie Biotherapeutics Inc., Redwood Ctiy, CA (US); The Cleveland Clinic, Cleveland, OH (US)

( * ) Notice: Subject to any disclaimer, the term of this patent is extended or adjusted under 35 U.S.C. 154(b) by 118 days.

(21) Appl. No.: 13/126,754

(22) PCT Filed: Oct. 29, 2009

(86) PCT No.: PCT/US2009/062648
§ 371 (c)(1),
(2), (4) Date: Apr. 28, 2011

(87) PCT Pub. No.: WO2010/051391
PCT Pub. Date: May 6, 2010

(65) Prior Publication Data
US 2011/0206701 A1    Aug. 25, 2011

Related U.S. Application Data

(60) Provisional application No. 61/110,295, filed on Oct. 31, 2008, provisional application No. 61/118,244, filed on Nov. 26, 2008.

(51) Int. Cl.
*A61K 39/395* (2006.01)

(52) U.S. Cl.
USPC ............... 424/133.1; 424/138.1; 424/178.1

(58) Field of Classification Search
None
See application file for complete search history.

(56) References Cited

U.S. PATENT DOCUMENTS

| | | | |
|---|---|---|---|
| 7,041,499 B2 | 5/2006 | Mathew et al. | |
| 7,709,610 B2 | 5/2010 | Williams et al. | |
| 8,008,450 B2 | 8/2011 | Williams et al. | |
| 8,088,898 B2 | 1/2012 | Williams et al. | |
| 8,133,981 B2 | 3/2012 | Williams et al. | |
| 8,349,330 B2 | 1/2013 | Williams et al. | |
| 8,436,146 B2 | 5/2013 | Williams et al. | |
| 8,444,980 B2 | 5/2013 | Williams et al. | |
| 8,445,646 B2 | 5/2013 | Williams et al. | |
| 8,461,306 B2 | 6/2013 | Williams et al. | |
| 2002/0123617 A1 | 9/2002 | Starling et al. | |
| 2003/0113332 A1 | 6/2003 | Mathew et al. | |
| 2004/0265315 A1* | 12/2004 | Dingivan et al. | 424/155.1 |
| 2005/0025763 A1 | 2/2005 | Williams et al. | |
| 2006/0057148 A1* | 3/2006 | Ashkenazi et al. | 424/155.1 |
| 2009/0238827 A1 | 9/2009 | Williams et al. | |

FOREIGN PATENT DOCUMENTS

| | | |
|---|---|---|
| WO | WO 01/46260 A2 | 6/2001 |
| WO | WO 2004/029207 A2 | 4/2004 |
| WO | WO 2008/019376 A2 | 2/2008 |

OTHER PUBLICATIONS

Paul, Fundamental Immunology, 3rd Edition, 1993, pp. 292-295.*
Rudikoff et al(Proc. Natl. Acad. Sci. USA 1982 vol. 79: p. 1979).*
Pascalis et al (The Journal of Immunology (2002) 169, 3076-3084).*
Casset et al. (2003) BBRC 307, 198-205.*
Brown et al (J. Immunol. May 1996; 156(9):3285-3291.*
Vajdos et al (J. Mol. Biol. Jul. 5, 2002;320(2); 415-428).*
Hsi et al, Clin. Cancer Res. vol. 14(9) May 1, 20089 p. 2775.*
Bouchon et al. (2001) "Cutting edge: activation of NK cell-mediated cytotoxicity by a SAP-independent receptor of the CD2 family"; *Journal of Immunology*, 167:5517-5521.
Genbank accession AB027233 (May 1999).
Genbank accession AF291815 (Aug. 2000).
Genbank accession AF390894 (Jun. 2001).
Genbank accession AF467909 (Jan 2002).
Genbank accession AJ271869 (Mar. 2000).
Genbank accession H73135 (Oct. 1995).
Genbank accession H74227 (Oct. 1995).
Genbank accession NM_021181 (Mar. 2005).
Hsi et al., "CS-1 is Expressed in Nasal Type NK/T Cell Lymphomas: Implications for Targeted Therapy with Elotuzumab (HuLuc63)" *Blood* (ASH Annual Meeting Abstracts) 112: Abstract 1779 (2008).
Hsi et al., "CS-1 is Expressed in Nasal Type NK/T Cell Lymphomas: Implications for Targeted Therapy with Elotuzumab (HuLuc63)" Retrieved from the Internet: URL:http://facebiotech.com/images/uploads/pdfs/SH2008_Hsiposter_final.pdf (2010).
Liang et al., "Natural Killer Cell Neoplasms," *Cancer* vol. 112, No. 7, pp. 1425-1436 (2008).
Wulf et al., "CD45 monoclonal antibody-mediated cytolysis of human NK and T lymphoma cells," *Haematologica* vol. 91, No. 7, pp. 886-894 (2006).
Halene, et al., "Sustained remission from angioimmunoblastic T-cell lymphoma induced by alentuzumab," *Nature Clinical Practice Oncology* vol. 3, No. 3, pp. 165-168 (2006).
Gallamini et al., "Alemtuzumab (Campath-1H) and CHOP chemotherapy as first-line treatment of peripheral T-cell lymphoma: results of a GITIL (Gruppo Italiano Terapie Innovative nei Linfomi) prospective multicenter trial," *Blood* vol. 110, No. 7, pp. 2316-2323 (2007).
Chen et al., "Beyond the Guidelines in the Treatm ent of Peripheral T-Cell Lymphoma: New Drug Development," *Journal of the National Comprehensive Cancer Network* vol. 6, No. 4, pp. 428-438 (2008).
Tai et al., "Anti-CS1 humanized monoclonal antibody HuLuc63 inhibits myeloma cell adhesion and induces antibody-dependent cellular cytotoxicity in the bone marrow milieu," *Blood* vol. 112, No. 4, pp. 1329-1337 (2008).
Greer, J.P., "Therapy of Peripheral T/NK Neoplasms," *Hematology* pp. 331-337 (2006).
International Search Report and Written Opinion dated Apr. 9, 2010 in correction with corresponding International application No. PCT/US2009/062648, pp. 1-18.
Paul, *Fundamental Immunology*, 3rd I Edition, 1993, pp. 292-295.
Rudikoff et al., "Single amino acid substitution altering antigenbinding specificity," *Proc. Natl. Acad. Sci. USA*, vol. 79, pp. 1979-1983 (1992).

(Continued)

*Primary Examiner* — Sheela J Huff
(74) *Attorney, Agent, or Firm* — Dechert LLP

(57) ABSTRACT

Uses of anti-CS1 antibodies, alone or in combination with other agents, for the treatment of rare lymphomas, such as NK lymphomas, NK/T-cell lymphomas, and angioimmunoblastic lymphomas.

30 Claims, 6 Drawing Sheets

(56) References Cited

OTHER PUBLICATIONS

De Pascalis et al., "Grafting of "Abbreviated" Complementary-Determining Regions Containing Specificity-Determining Residues Essential for Ligand Contact to Engineer a Less Immunogenic Humanized Monoclonal Antibody," *The Journal of Immunology*, vol. 169, pp. 3076-3084 (2002).

Casset et al. "A peptide mimetic of an anti-CD4 monoclonal antibody by rational design," *Biochemical and Biophysical Research Communications* vol. 307 (2003) pp. 198-205.

Brown et al., "Tolerance of single, but not multiple amino acid replacements in antibody VH CDR 2: a means of minimizing B cell wastage from somatic hypermutation?" *The Journal of Immunology* vol. 156, pp. 3285-3291 (1996).

Vajdos, et al, "Comprehensive Functional Maps of the Antigen-binding Site of an Anti-ErbB2 Antibody Obtained with Shotgun Scanning Mutagenesis," *J. Mol. Biol.*, vol. 320, pp. 415-428 (2002).

Hsi et al., "CS1, a Potential New Therapeutic Antibody Target for the Treatment of Multiple Myeloma," *Clinical Cancer Research* 2008:14(9), pp. 2775-2784.

\* cited by examiner

Figure 2A
Figure 2B
Figure 2C

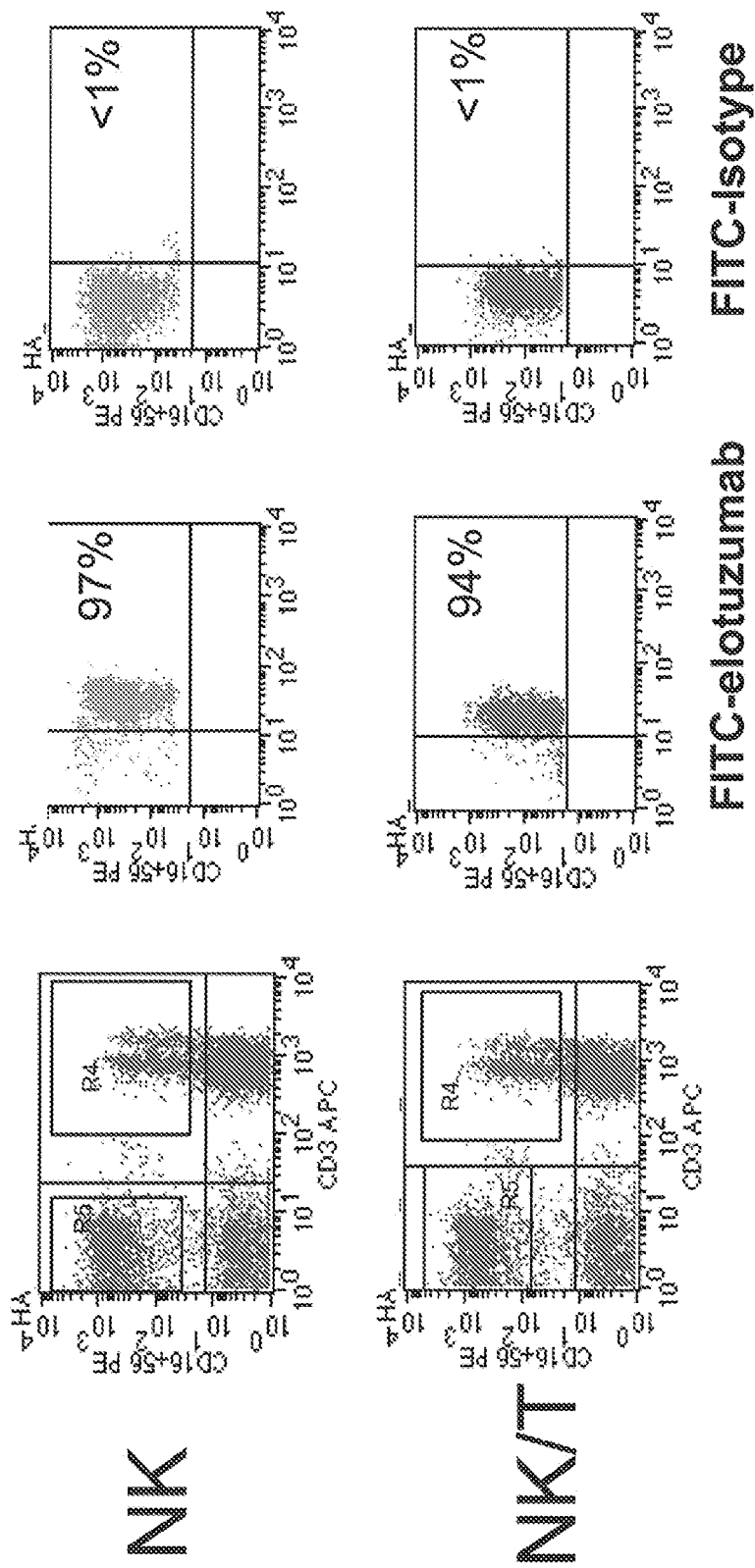

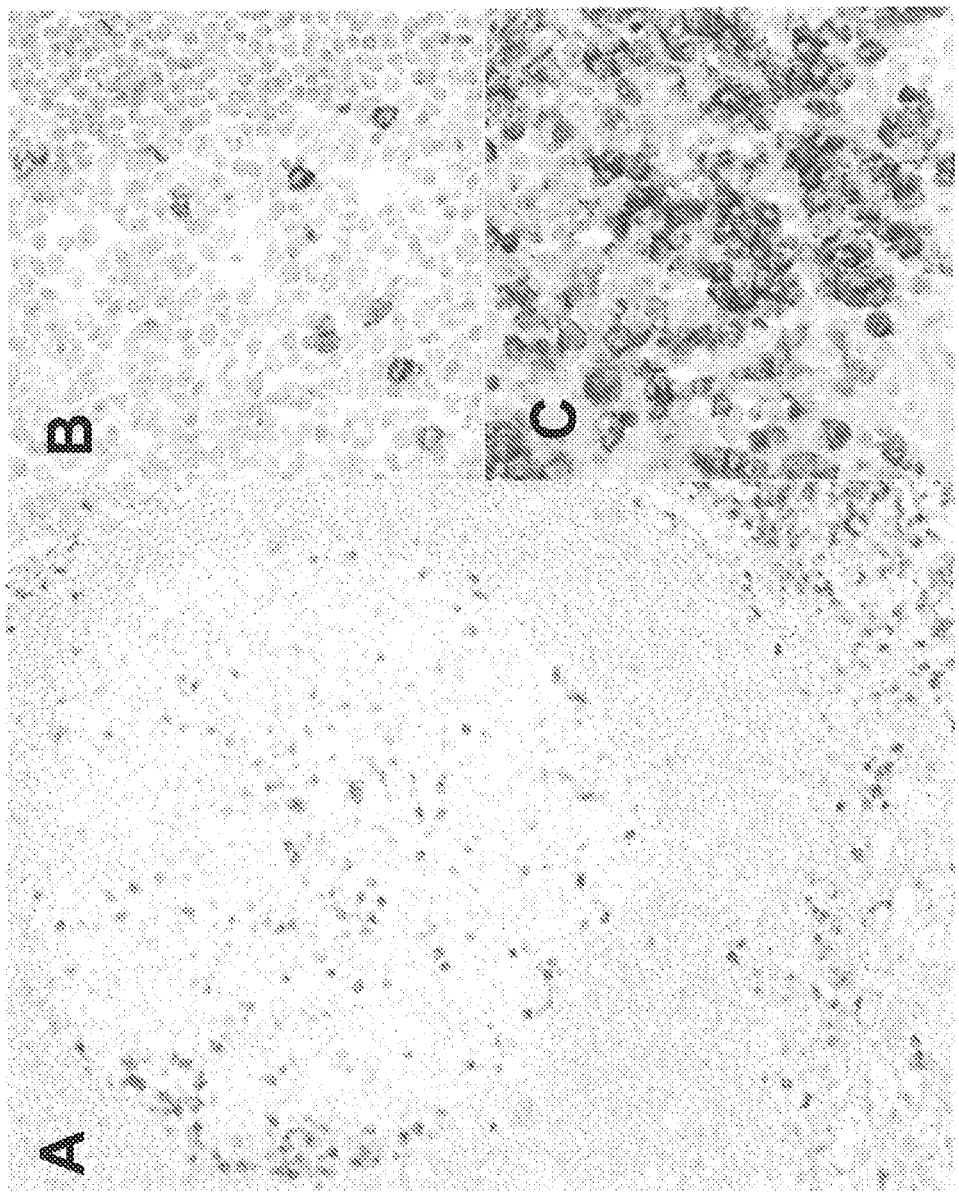
Figure 4: CS1(1G9) expression in tonsil

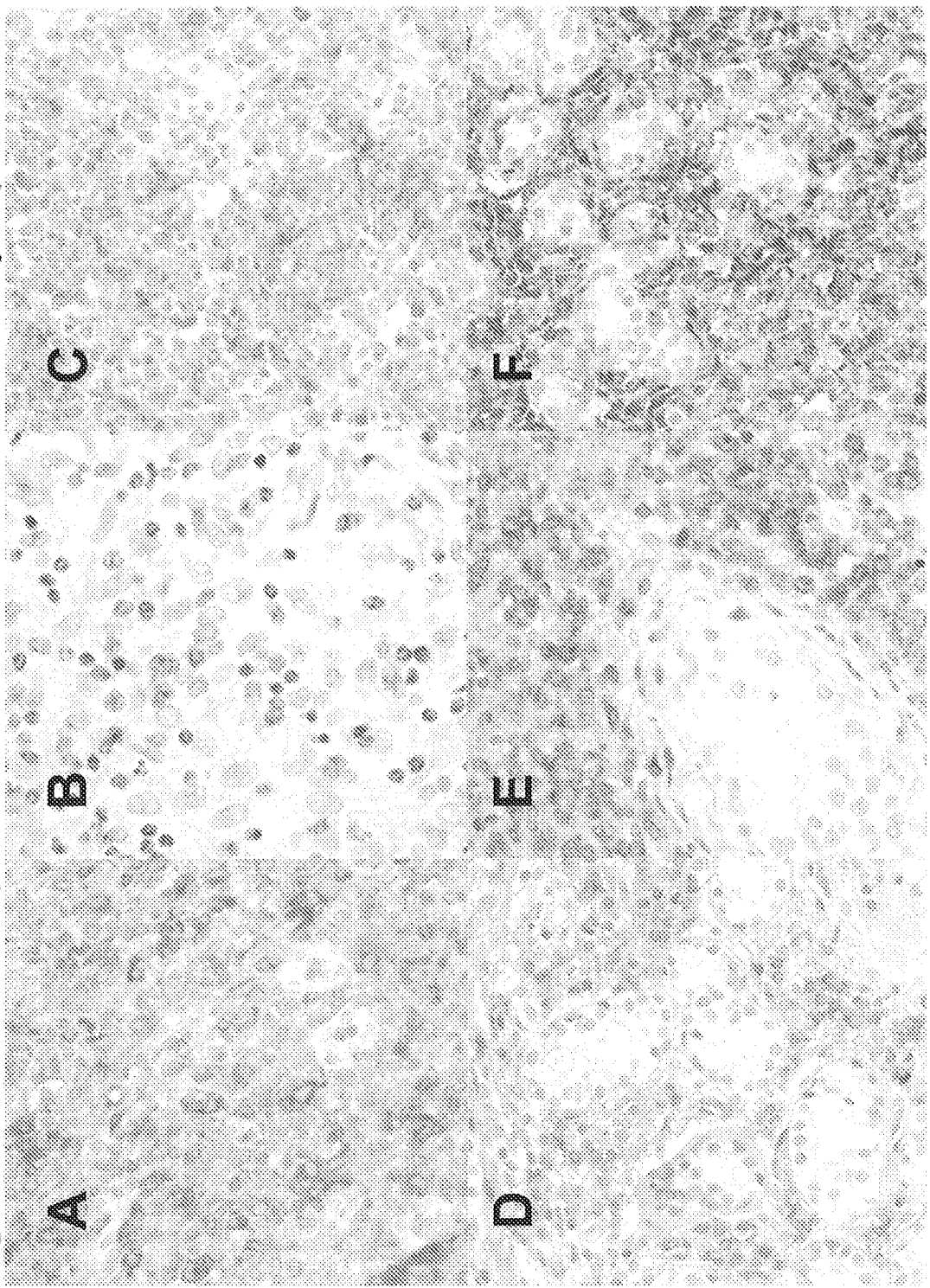

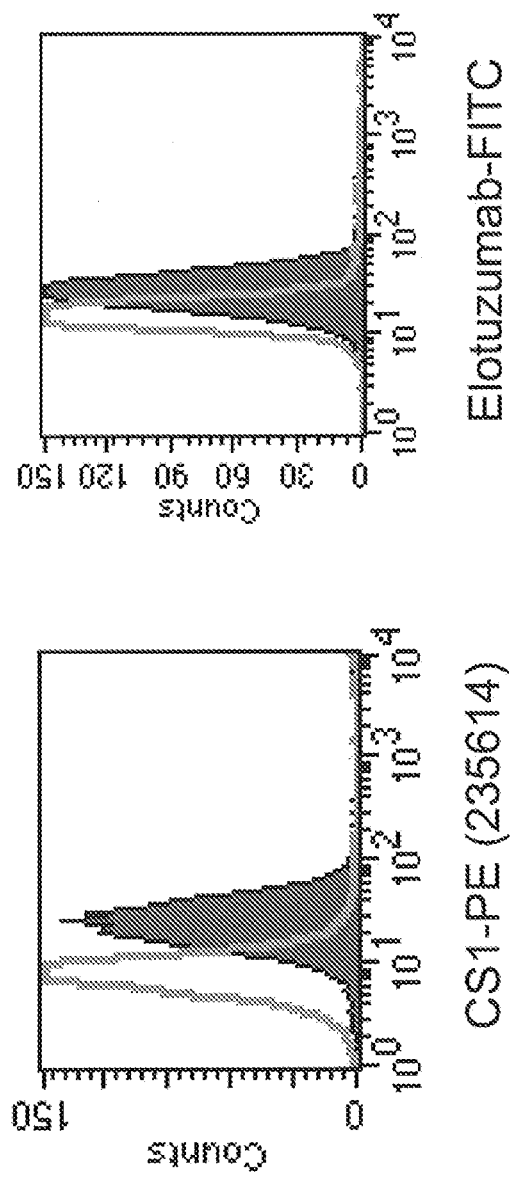

SEQUENCE LISTING

<160> NUMBER OF SEQ ID NOS: 40

<210> SEQ ID NO 1
<211> LENGTH: 119
<212> TYPE: PRT
<213> ORGANISM: Homo sapiens

<400> SEQUENCE: 1

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg Pro Asp Gly Asn Tyr Trp Tyr Phe Asp Val Trp Gly Ala Gly
            100                 105                 110

Thr Thr Val Thr Val Ser Ser
        115

<210> SEQ ID NO 2
<211> LENGTH: 107
<212> TYPE: PRT
<213> ORGANISM: Homo sapiens

<400> SEQUENCE: 2

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Ile Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys
            100                 105

<210> SEQ ID NO 3
<211> LENGTH: 5
<212> TYPE: PRT
<213> ORGANISM: Homo sapiens

<400> SEQUENCE: 3

Arg Tyr Trp Met Ser
1               5

<210> SEQ ID NO 4
<211> LENGTH: 17
<212> TYPE: PRT

-continued

<213> ORGANISM: Homo sapiens

<400> SEQUENCE: 4

Glu Ile Asn Pro Asp Ser Ser Thr Ile Asn Tyr Thr Pro Ser Leu Lys
1               5                   10                  15

Asp

<210> SEQ ID NO 5
<211> LENGTH: 10
<212> TYPE: PRT
<213> ORGANISM: Homo sapiens

<400> SEQUENCE: 5

Pro Asp Gly Asn Tyr Trp Tyr Phe Asp Val
1               5                   10

<210> SEQ ID NO 6
<211> LENGTH: 11
<212> TYPE: PRT
<213> ORGANISM: Homo sapiens

<400> SEQUENCE: 6

Lys Ala Ser Gln Asp Val Gly Ile Ala Val Ala
1               5                   10

<210> SEQ ID NO 7
<211> LENGTH: 7
<212> TYPE: PRT
<213> ORGANISM: Homo sapiens

<400> SEQUENCE: 7

Trp Ala Ser Thr Arg His Thr
1               5

<210> SEQ ID NO 8
<211> LENGTH: 9
<212> TYPE: PRT
<213> ORGANISM: Homo sapiens

<400> SEQUENCE: 8

Gln Gln Tyr Ser Ser Tyr Pro Tyr Thr
1               5

<210> SEQ ID NO 9
<211> LENGTH: 119
<212> TYPE: PRT
<213> ORGANISM: Homo sapiens

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Asp Gly Asn Tyr Trp Tyr Phe Asp Val Trp Gly Gln Gly

```
              100                 105                 110
Thr Leu Val Thr Val Ser Ser
        115

<210> SEQ ID NO 10
<211> LENGTH: 107
<212> TYPE: PRT
<213> ORGANISM: Homo sapiens

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Ser Tyr Pro Tyr
                85                  90                  95

Thr Phe Gly Gln Gly Thr Lys Val Glu Ile Lys
            100                 105

<210> SEQ ID NO 11
<211> LENGTH: 5
<212> TYPE: PRT
<213> ORGANISM: Homo sapiens

<400> SEQUENCE: 11

Arg Tyr Trp Met Ser
1               5

<210> SEQ ID NO 12
<211> LENGTH: 17
<212> TYPE: PRT
<213> ORGANISM: Homo sapiens

<400> SEQUENCE: 12

Glu Ile Asn Pro Asp Ser Ser Thr Ile Asn Tyr Ala Pro Ser Leu Lys
1               5                   10                  15

Asp

<210> SEQ ID NO 13
<211> LENGTH: 10
<212> TYPE: PRT
<213> ORGANISM: Homo sapiens

<400> SEQUENCE: 13

Pro Asp Gly Asn Tyr Trp Tyr Phe Asp Val
1               5                   10

<210> SEQ ID NO 14
<211> LENGTH: 11
<212> TYPE: PRT
<213> ORGANISM: Homo sapiens

<400> SEQUENCE: 14

Lys Ala Ser Gln Asp Val Gly Ile Ala Val Ala
1               5                   10
```

<210> SEQ ID NO 15
<211> LENGTH: 7
<212> TYPE: PRT
<213> ORGANISM: Homo sapiens

<400> SEQUENCE: 15

Trp Ala Ser Thr Arg His Thr
1               5

<210> SEQ ID NO 16
<211> LENGTH: 9
<212> TYPE: PRT
<213> ORGANISM: Homo sapiens

<400> SEQUENCE: 16

Gln Gln Tyr Ser Ser Tyr Pro Tyr Thr
1               5

<210> SEQ ID NO 17
<211> LENGTH: 120
<212> TYPE: PRT
<213> ORGANISM: Homo sapiens

<400> SEQUENCE: 17

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Ser Phe Thr Thr Tyr
                20                  25                  30

Trp Met Asn Trp Val Lys Gln Arg Pro Gly Gln Gly Leu Glu Trp Ile
            35                  40                  45

Gly Met Ile His Pro Ser Asp Ser Glu Thr Arg Leu Asn Gln Lys Phe
        50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Arg Ser Thr Met Ile Ala Thr Arg Ala Met Asp Tyr Trp Gly Gln
            100                 105                 110

Gly Thr Ser Val Thr Val Ser Ser
        115                 120

<210> SEQ ID NO 18
<211> LENGTH: 107
<212> TYPE: PRT
<213> ORGANISM: Homo sapiens

<400> SEQUENCE: 18

Asp Ile Val Met Thr Gln Ser Gln Lys Ser Met Ser Thr Ser Val Gly
1               5                   10                  15

Asp Arg Val Ser Ile Thr Cys Lys Ala Ser Gln Asp Val Ile Thr Gly
                20                  25                  30

Val Ala Trp Tyr Gln Gln Lys Pro Gly Gln Ser Pro Lys Leu Leu Ile
            35                  40                  45

Tyr Ser Ala Ser Tyr Arg Tyr Thr Gly Val Pro Asp Arg Phe Thr Gly
        50                  55                  60

Ser Gly Ser Gly Thr Asp Phe Thr Phe Thr Ile Ser Asn Val Gln Ala
65                  70                  75                  80

Glu Asp Leu Ala Val Tyr Tyr Cys Gln Gln His Tyr Ser Thr Pro Leu
                85                  90                  95

```
Thr Phe Gly Ala Gly Thr Lys Leu Glu Leu Lys
            100                 105
```

<210> SEQ ID NO 19
<211> LENGTH: 5
<212> TYPE: PRT
<213> ORGANISM: Homo sapiens

<400> SEQUENCE: 19

```
Thr Tyr Trp Met Asn
1               5
```

<210> SEQ ID NO 20
<211> LENGTH: 17
<212> TYPE: PRT
<213> ORGANISM: Homo sapiens

<400> SEQUENCE: 20

```
Met Ile His Pro Ser Asp Ser Glu Thr Arg Leu Asn Gln Lys Phe Lys
1               5                   10                  15

Asp
```

<210> SEQ ID NO 21
<211> LENGTH: 11
<212> TYPE: PRT
<213> ORGANISM: Homo sapiens

<400> SEQUENCE: 21

```
Ser Thr Met Ile Ala Thr Arg Ala Met Asp Tyr
1               5                   10
```

<210> SEQ ID NO 22
<211> LENGTH: 11
<212> TYPE: PRT
<213> ORGANISM: Homo sapiens

<400> SEQUENCE: 22

```
Lys Ala Ser Gln Asp Val Ile Thr Gly Val Ala
1               5                   10
```

<210> SEQ ID NO 23
<211> LENGTH: 7
<212> TYPE: PRT
<213> ORGANISM: Homo sapiens

<400> SEQUENCE: 23

```
Ser Ala Ser Tyr Arg Tyr Thr
1               5
```

<210> SEQ ID NO 24
<211> LENGTH: 9
<212> TYPE: PRT
<213> ORGANISM: Homo sapiens

<400> SEQUENCE: 24

```
Gln Gln His Tyr Ser Thr Pro Leu Thr
1               5
```

<210> SEQ ID NO 25
<211> LENGTH: 121
<212> TYPE: PRT
<213> ORGANISM: Homo sapiens

<400> SEQUENCE: 25

```
Gln Val Gln Leu Gln Gln Ser Gly Ala Glu Leu Ala Arg Pro Gly Ala
```

```
                 1               5                  10                 15
Ser Val Lys Leu Ser Cys Lys Ala Ser Gly Tyr Thr Phe Thr Ser Tyr
                    20                 25                 30

Trp Met Gln Trp Val Lys Gln Arg Pro Gly Gln Gly Leu Glu Trp Ile
        35                 40                 45

Gly Ala Ile Tyr Pro Gly Asp Gly Asp Thr Arg Tyr Thr Gln Lys Phe
    50                 55                 60

Lys Gly Lys Ala Thr Leu Thr Ala Asp Lys Ser Ser Thr Ala Tyr
65                  70                 75                 80

Met Gln Leu Ser Ser Leu Ala Ser Glu Asp Ser Ala Val Tyr Tyr Cys
                85                 90                 95

Ala Arg Gly Lys Val Tyr Tyr Gly Ser Asn Pro Phe Ala Tyr Trp Gly
            100                105                110

Gln Gly Thr Leu Val Thr Val Ser Ala
            115                120
```

<210> SEQ ID NO 26
<211> LENGTH: 107
<212> TYPE: PRT
<213> ORGANISM: Homo sapiens

<400> SEQUENCE: 26

```
Asp Ile Gln Met Thr Gln Ser Ser Tyr Leu Ser Val Ser Leu Gly
1                5                  10                 15

Gly Arg Val Thr Ile Thr Cys Lys Ala Ser Asp His Ile Asn Asn Trp
                20                 25                 30

Leu Ala Trp Tyr Gln Gln Lys Pro Gly Asn Ala Pro Arg Leu Leu Ile
        35                 40                 45

Ser Gly Ala Thr Ser Leu Glu Thr Gly Val Pro Ser Arg Phe Ser Gly
    50                 55                 60

Ser Gly Ser Gly Lys Asp Tyr Thr Leu Ser Ile Thr Ser Leu Gln Thr
65                  70                 75                 80

Glu Asp Val Ala Thr Tyr Tyr Cys Gln Gln Tyr Trp Ser Thr Pro Trp
                85                 90                 95

Thr Phe Gly Gly Gly Thr Lys Leu Glu Ile Lys
            100                105
```

<210> SEQ ID NO 27
<211> LENGTH: 5
<212> TYPE: PRT
<213> ORGANISM: Homo sapiens

<400> SEQUENCE: 27

```
Ser Tyr Trp Met Gln
1                5
```

<210> SEQ ID NO 28
<211> LENGTH: 17
<212> TYPE: PRT
<213> ORGANISM: Homo sapiens

<400> SEQUENCE: 28

```
Ala Ile Tyr Pro Gly Asp Gly Asp Thr Arg Tyr Thr Gln Lys Phe Lys
1                5                  10                 15

Gly
```

<210> SEQ ID NO 29
<211> LENGTH: 12
<212> TYPE: PRT

<213> ORGANISM: Homo sapiens

<400> SEQUENCE: 29

Gly Lys Val Tyr Tyr Gly Ser Asn Pro Phe Ala Tyr
1               5                   10

<210> SEQ ID NO 30
<211> LENGTH: 11
<212> TYPE: PRT
<213> ORGANISM: Homo sapiens

<400> SEQUENCE: 30

Lys Ala Ser Asp His Ile Asn Asn Trp Leu Ala
1               5                   10

<210> SEQ ID NO 31
<211> LENGTH: 7
<212> TYPE: PRT
<213> ORGANISM: Homo sapiens

<400> SEQUENCE: 31

Gly Ala Thr Ser Leu Glu Thr
1               5

<210> SEQ ID NO 32
<211> LENGTH: 9
<212> TYPE: PRT
<213> ORGANISM: Homo sapiens

<400> SEQUENCE: 32

Gln Gln Tyr Trp Ser Thr Pro Trp Thr
1               5

<210> SEQ ID NO 33
<211> LENGTH: 120
<212> TYPE: PRT
<213> ORGANISM: Mus musculus

<400> SEQUENCE: 33

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Met Asn Trp Val Lys Gln Arg Pro Gly Gln Gly Leu Glu Trp Ile
        35                  40                  45

Gly Arg Ile Tyr Pro Gly Asp Gly Asp Thr Lys Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Val Asp Ser Ala Val Tyr Phe Cys
                85                  90                  95

Ala Arg Ser Thr Met Ile Ala Thr Gly Ala Met Asp Tyr Trp Gly Gln
                100                 105                 110

Gly Thr Ser Val Thr Val Ser Ser
            115                 120

<210> SEQ ID NO 34
<211> LENGTH: 108
<212> TYPE: PRT
<213> ORGANISM: Mus musculus

<400> SEQUENCE: 34

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Pro
                85                  90                  95

Tyr Thr Phe Gly Gly Gly Thr Lys Leu Glu Ile Lys
            100                 105
```

<210> SEQ ID NO 35
<211> LENGTH: 5
<212> TYPE: PRT
<213> ORGANISM: Mus musculus

<400> SEQUENCE: 35

```
Ser Ser Trp Met Asn
1               5
```

<210> SEQ ID NO 36
<211> LENGTH: 17
<212> TYPE: PRT
<213> ORGANISM: Mus musculus

<400> SEQUENCE: 36

```
Arg Ile Tyr Pro Gly Asp Gly Asp Thr Lys Tyr Asn Gly Lys Phe Lys
1               5                   10                  15

Gly
```

<210> SEQ ID NO 37
<211> LENGTH: 11
<212> TYPE: PRT
<213> ORGANISM: Mus musculus

<400> SEQUENCE: 37

```
Ser Thr Met Ile Ala Thr Gly Ala Met Asp Tyr
1               5                   10
```

<210> SEQ ID NO 38
<211> LENGTH: 11
<212> TYPE: PRT
<213> ORGANISM: Mus musculus

<400> SEQUENCE: 38

```
Lys Ala Ser Gln Asp Val Ser Thr Ala Val Ala
1               5                   10
```

<210> SEQ ID NO 39
<211> LENGTH: 7
<212> TYPE: PRT
<213> ORGANISM: Mus musculus

<400> SEQUENCE: 39

```
Ser Ala Ser Tyr Arg Tyr Thr
1               5
```

<210> SEQ ID NO 40

```
<211> LENGTH: 10
<212> TYPE: PRT
<213> ORGANISM: Mus musculus

<400> SEQUENCE: 40

Gln Gln His Tyr Ser Thr Pro Pro Tyr Thr
1               5                   10
```

USE OF ANTI-CS1 ANTIBODIES FOR TREATMENT OF RARE LYMPHOMAS

CROSS REFERENCE TO RELATED APPLICATION

This application claims the priority benefit under 35 U.S.C. §119(e) of U.S. Provisional Application No. 61/110,295, filed on Oct. 31, 2008, and U.S. Provisional Application No. 61/118,244, filed on Nov. 26, 2008, the contents of each of which is incorporated by reference herein in its entirety.

1. FIELD OF THE INVENTION

The present invention relates to the use of anti-CS1 antibodies for the treatment of NK lymphomas, NK/T-cell lymphomas, and angioimmunoblastic lymphomas.

2. BACKGROUND

CS1 (CD2-subset 1), also known as SLAMF7, CRACC, 19A, APEX-I, and FOAP12 (Genbank Accession Number NM_021181.3), is member of the CD2 family of cell surface glycoproteins. CS1 is not expressed on normal tissues nor on $CD34^+$ stem cells but its expression has been reported on primary myeloma, natural killer cells, cytotoxic t cells and activated B cells.

Non-Hodgkin's lymphomas are cancers of lymphoid tissue (lymph nodes, spleen, and other organs of the immune system). Non-Hodgkin's lymphomas include slow-growing lymphomas, moderately aggressive lymphomas and aggressive lymphomas of B-cell, T-cell origin, or natural killer (NK)-cell origin. For example, angioimmunoblastic lymphomas are moderately aggressive lymphomas that constitute 1-2% of Non-Hodgkin's lymphomas. Patients with this disease usually present at an advanced stage and show systemic involvement. Although steroid therapy is initially beneficial in many patients, the disease usually progresses to another form of lymphoma (e.g., to high-grade T-cell immunoblastic lymphoma or Epstein-Barr virus positive diffuse large B-cell lymphoma).

T/NK and NK-cell lymphomas are rare forms of non-Hodgkin's lymphomas that are more common among Asians in comparison to other ethnic groups. These lymphomas develop mostly in the nasal cavity and occasionally in other sites, such as the skin and intestinal tract. Most tumors show NK-cell, and occasionally T-cell, phenotypes. Extranodal NK/T-cell lymphomas are uncommon neoplasms that are highly aggressive and show a strong association with Epstein-Barr virus (EBV), which is considered to be an etiologic agent of these tumors. To this date, there is no satisfactory therapy for advanced forms of these lymphomas.

Thus, there is still a need for new therapies and therapeutic regimens for treating rare lymphomas such as NK lymphomas, NK/T-cell lymphomas, and angioimmunoblastic T-cell lymphomas.

Citation or identification of any reference in Section 2 or in any other section of this application shall not be construed as an admission that such reference is available as prior art to the present invention.

3. SUMMARY

CS1 (CRACC, SLAMF7, CD319) is a member of the signaling lymphocyte activating molecule-related receptor family. It is highly and uniformly expressed on the cell surface of benign and malignant plasma cells. Lower levels of CS1 have also been reported on NK cells and NK-like T-cells (NK/T). CS1 expression in NK and T-cell lymphomas-aggressive lymphomas for which no effective therapy exists—was heretofore unknown. The expression of CS1 in NK and peripheral T-cell lymphomas as compared to normal NK and T cells was determined. In contrast to the low expression levels of CS1 on normal NK cells and NK-like T-cells (NK/T), CS1 is highly expressed in NK and peripheral T-cell lymphomas. Targeting CS1 in other cancerous cell types has been shown to inhibit the proliferation of cancer cells. For example, CS1 is highly expressed on myeloma cells and HuLuc63, an anti-CS1 antibody, exhibits in vitro antibody-dependent cellular cytotoxicity (ADCC) in primary myeloma cells and in vivo anti-tumor activity (Hsi et al., 2008, Clin. Cancer Res. 14(9):2775-84).

Accordingly, methods of treating NK cell lymphoma, NK/T cell lymphoma and angioimmunoblastic T-cell lymphoma by administering to a patient in need thereof a therapeutically effective amount of an anti-CS1 antibody or antigen binding fragment thereof, or an anti-CS1 antibody-drug conjugate are described herein. The anti-CS1 antibodies, fragments and conjugates can be administered as monotherapies or in combinations with other therapeutic agents, for example in combination with the standard of care therapy for the corresponding class of lymphoma. Specific therapeutic regimens are provided herein. Patients with NK cell lymphoma, NK/T cell lymphoma or angioimmunoblastic T-cell lymphoma at any stage can benefit from treatment in accordance with the methods described herein.

All publications mentioned in this specification are herein incorporated by reference. Any discussion of documents, acts, materials, devices, articles or the like that has been included in this specification is solely for the purpose of providing a context for the present disclosure. It is not to be taken as an admission that any or all of these matters form part of the prior art base or were common general knowledge in the field relevant to the present disclosure as it existed anywhere before the priority date of this application.

The features and advantages of the disclosure will become further apparent from the following detailed description of embodiments thereof.

It should be noted that the indefinite articles "a" and "an" and the definite article "the" are used in the present application, as is common in patent applications, to mean one or more unless the context clearly dictates otherwise. Further, the term "or" is used in the present application, as is common in patent applications, to mean the disjunctive "or" or the conjunctive "and."

4. BRIEF DESCRIPTION OF THE FIGURES

FIGS. 1A-1B are examples of immunohistochemistry demonstrating CS1 expression in peripheral non-Hodgkin's T-cell lymphoma (FIG. 1A) and angioimmunoblastic non-Hodgkin's T-cell lymphoma (FIG. 1B). IHC score was 3+ for both samples. Anti-CS1 antibody 1G9 was used for the detection of CS1.

FIGS. 2A-2C are examples of immunohistochemistry demonstrating CS1 expression in NK/T-cell lymphoma at 40× (FIG. 2A) and at 10× (FIG. 2B) magnification, with FIG. 2C showing immunohistochemistry with a negative control antibody. IHC score for the sample shown in FIGS. 2A-2B was 4+. Anti-CS1 antibody 1G9 was used for the detection of CS1; the negative control antibody was MsIgG1.

FIG. 3 shows the results of flow cytometry experiments to detect expression of CS1. CS1 is expressed in the majority of NK cells (upper panels) and NK-like T-cells (lower panels).

FIG. 4 shows CS1 expression in normal tonsil.

FIG. 5 shows CS1 expression in T-cell lymphoma and NK lymphoma.

FIG. 6 shows CS1 expression the HANK1 NK/T-cell lymphoma cell line.

5. DETAILED DESCRIPTION

5.1 Anti-CS1 Antibodies

Figure 1A:
Figure 1B:
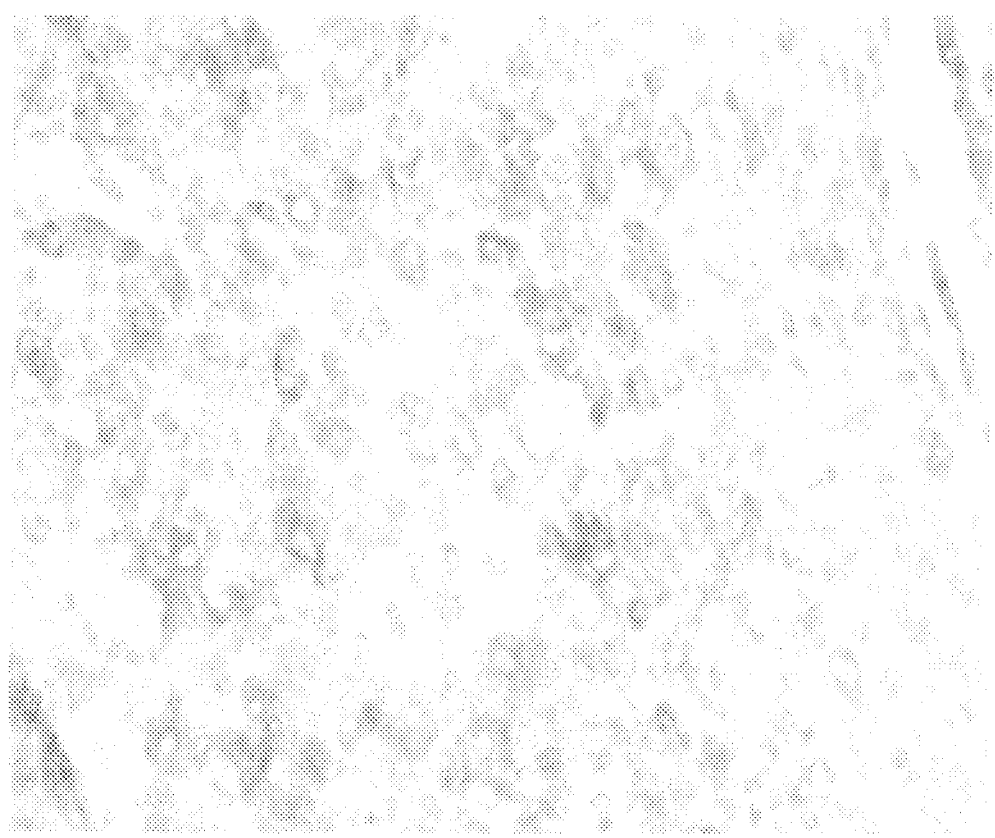

The present disclosure relates to the use of anti-CS1 antibodies to treat rare lymphomas such as NK/T-cell lymphomas. Unless indicated otherwise, the term "antibody" (Ab) refers to an immunoglobulin molecule that specifically binds to, or is immunologically reactive with, a particular antigen, and includes polyclonal, monoclonal, genetically engineered and otherwise modified forms of antibodies, including but not limited to chimeric antibodies, humanized antibodies, heteroconjugate antibodies (e.g., bispecific antibodies, diabodies, triabodies, and tetrabodies), and antigen binding fragments of antibodies, including e.g., Fab', F(ab')$_2$, Fab, Fv, rIgG, and scFv fragments. Moreover, unless otherwise indicated, the term "monoclonal antibody" (mAb) is meant to include both intact molecules, as well as, antibody fragments (such as, for example, Fab and F(ab')$_2$ fragments) which are capable of specifically binding to a protein. Fab and F(ab')$_2$ fragments lack the Fc fragment of intact antibody, clear more rapidly from the circulation of the animal or plant, and may have less non-specific tissue binding than an intact antibody (Wahl et al., 1983, J. Nucl. Med. 24:316).

Anti-CS1 antibodies that are suitable for use in the methods of the treatment disclosed herein include, but are not limited to, isolated antibodies that bind one or more of the three epitope clusters identified on CS1 and monoclonal antibodies produced by the hybridoma cell lines: Luc2, Luc3, Luc15, Luc22, Luc23, Luc29, Luc32, Luc34, Luc35, Luc37, Luc38, Luc39, Luc56, Luc60, Luc63, Luc69, LucX.1, LucX.2 or Luc90. These monoclonal antibodies are named as the antibodies: Luc2, Luc3, Luc15, Luc22, Luc23, Luc29, Luc32, Luc34, Luc35, Luc37, Luc38, Luc39, Luc56, Luc60, Luc63, Luc69, LucX and Luc90, respectively, hereafter. Humanized versions are denoted by the prefix "hu" or "Hu" (see, e.g., U.S. Patent Publication Nos. 2005/0025763 and 2006/0024296, the contents of which are incorporated herein by reference).

In certain embodiments, suitable anti-CS1 antibodies include antibodies that bind one or more of the three epitope clusters identified on CS1 (see, e.g., U.S. Patent Publication No. 2006/0024296, the content of which is incorporated herein by reference). As disclosed in U.S. Patent Publication No. 2006/0024296, the CS1 antibody binding sites have been grouped into 3 epitope clusters:

the epitope cluster defined by Luc90, which binds to hu50/mu50. This epitope covers from about amino acid residue 23 to about amino acid residue 151 of human CS1. This epitope is resided within the domain 1 (V domain) of the extracellular domain. This epitope is also recognized by Luc34, LucX (including LucX$_1$ and LucX$_2$) and Luc69;

the epitope cluster defined by Luc38, which binds to mu25/hu75 and hu50/mu50. This epitope likely covers from about amino acid residue 68 to about amino acid residue 151 of human CS1. This epitope is also recognized by Luc5; and the epitope cluster defined by Luc63, which binds to mu75/hu25. This epitope covers from about amino acid residue 170 to about amino acid residue 227 of human CS1. This epitope is resided within domain 2 (C2 domain) of human CS1. This epitope is also recognized by Luc4, Luc 12, Luc23, Luc29, Luc32 and Luc37.

In a specific example, the anti-CS1 antibody used in the present methods is Luc63 or comprises the light chain variable region and/or heavy chain variable region sequence of Luc63. The amino acid sequences for the heavy chain variable region and the light chain variable region for Luc63 are disclosed in U.S. Patent Publication No. 2005/0025763 as SEQ ID NO:5 and SEQ ID NO:6, respectively, the contents of which are incorporated herein by reference. The sequences of the heavy and light chain variable regions of Luc63 are represented herein by SEQ ID NO:1 and SEQ ID NO:2, respectively. In other aspects, the an anti-CS1 antibody used in the treatment of NK lymphomas, NK/T-cell lymphomas, or angioimmunoblastic lymphomas comprises the heavy chain CDR sequences, light chain CDR sequences, or both heavy and light chain CDR sequences of Luc63, or comprises one, two or three CDR sequences having at least 80%, at least 85%, or at least 90% sequence identity to the heavy chain CDR sequences, light chain CDR sequences, or both heavy and light chain CDR sequences of Luc63. The heavy chain CDR sequences of Luc63 are represented herein by SEQ ID NOS. 3, 4 and 5, and the light chain CDR sequence of Luc63 are represented herein by SEQ ID NOS. 6, 7 and 8.

In a specific example, the anti-CS1 antibody used in the present methods is HuLuc63 or comprises the light chain variable region and/or heavy chain variable region sequence of HuLuc63. The amino acid sequences for the heavy chain variable region and the light chain variable region for HuLuc63 are disclosed in U.S. Patent Publication No. 2006/0024296 as SEQ ID NO:41 and SEQ ID NO:44, respectively, the contents of which are incorporated herein by reference. The sequences of the heavy and light chain variable regions of HuLuc63 are represented herein by SEQ ID NO:9 and SEQ ID NO:10, respectively. In other aspects, the an anti-CS1 antibody used in the treatment of NK lymphomas, NK/T-cell lymphomas, or angioimmunoblastic lymphomas comprises the heavy chain CDR sequences, light chain CDR sequences, or both heavy and light chain CDR sequences of HuLuc63, or comprises one, two or three CDR sequences having at least 80%, at least 85%, or at least 90% sequence identity to the heavy chain CDR sequences, light chain CDR sequences, or both heavy and light chain CDR sequences of HuLuc63. The heavy chain CDR sequences of HuLuc63 are represented herein by SEQ ID NOS. 11, 12 and 13, and the light chain CDR sequence of HuLuc63 are represented herein by SEQ ID NOS. 14, 15 and 16.

In another specific example, the anti-CS1 antibody used in the present methods is Luc90 or comprises the light chain variable region and/or heavy chain variable region sequence of Luc90. The amino acid sequences for the heavy chain variable region and the light chain variable region for Luc90 are disclosed in U.S. Patent Publication No. 2005/0025763 as SEQ ID NO:3 and SEQ ID NO:4, respectively, the contents of which are incorporated herein by reference. The sequences of the heavy and light chain variable regions of Luc90 are represented herein by SEQ ID NO:17 and SEQ ID NO:18, respectively. In other aspects, the an anti-CS1 antibody used in the treatment of NK lymphomas, NK/T-cell lymphomas, or angioimmunoblastic lymphomas comprises the heavy chain CDR sequences, light chain CDR sequences, or both heavy and light chain CDR sequences of Luc90, or comprises one, two or three CDR sequences having at least 80%, at least 85%, or at least 90% sequence identity to the heavy chain CDR sequences, light chain CDR sequences, or both heavy and light chain CDR sequences of Luc90. The heavy chain CDR sequences of Luc90 are represented herein by SEQ ID NOS. 19, 20 and 21, and the light chain CDR sequence of Luc90 are represented herein by SEQ ID NOS. 22, 23 and 24.

In yet another specific example, the anti-CS1 antibody used in the present methods is Luc34 or comprises the light chain variable region and/or heavy chain variable region sequence of Luc34. The amino acid sequences for the heavy chain variable region and the light chain variable region for Luc34 are disclosed in U.S. Patent Publication No. 2005/0025763 as SEQ ID NO:7 and SEQ ID NO:8, respectively, the contents of which are incorporated herein by reference. The sequences of the heavy and light chain variable regions of Luc34 are represented herein by SEQ ID NO:25 and SEQ ID NO:26, respectively. In other aspects, the an anti-CS1 antibody used in the treatment of NK lymphomas, NK/T-cell lymphomas, or angioimmunoblastic lymphomas comprises the heavy chain CDR sequences, light chain CDR sequences, or both heavy and light chain CDR sequences of Luc34, or comprises one, two or three CDR sequences having at least 80%, at least 85%, or at least 90% sequence identity to the heavy chain CDR sequences, light chain CDR sequences, or both heavy and light chain CDR sequences of Luc34. The heavy chain CDR sequences of Luc34 are represented herein by SEQ ID NOS. 27, 28 and 29, and the light chain CDR sequence of Luc34 are represented herein by SEQ ID NOS. 30, 31 and 32.

In yet another specific example, the anti-CS1 antibody used in the present methods is the LucX antibody LucX.2 or comprises the light chain variable region and/or heavy chain variable region sequence of LucX.2. The amino acid sequences for the heavy chain variable region and the light chain variable region for LucX.2 are disclosed in U.S. Patent Publication No. 2006/0024296 as SEQ ID NO:66 and SEQ ID NO:67, respectively, the contents of which are incorporated herein by reference. The sequences of the heavy and light chain variable regions of LucX.2 are represented herein by SEQ ID NO:33 and SEQ ID NO:34, respectively. In other aspects, the an anti-CS1 antibody used in the treatment of NK lymphomas, NK/T-cell lymphomas, or angioimmunoblastic lymphomas comprises the heavy chain CDR sequences, light chain CDR sequences, or both heavy and light chain CDR sequences of LucX.2, or comprises one, two or three CDR sequences having at least 80%, at least 85%, or at least 90% sequence identity to the heavy chain CDR sequences, light chain CDR sequences, or both heavy and light chain CDR sequences of LucX.2. The heavy chain CDR sequences of LucX.2 are represented herein by SEQ ID NOS. 35, 36 and 37, and the light chain CDR sequence of LucX.2 are represented herein by SEQ ID NOS. 38, 39 and 40.

Table 1 below provides the sequences of HuLuc63, Luc90, Luc34 and LucX.2 identified above:

| SEQ ID NO. | Description | Sequence |
|---|---|---|
| 1 | Luc63 heavy chain variable region | Glu Val Lys Leu Leu Glu Ser Gly Gly Gly Leu Val Gln Pro Gly Gly Ser Leu Lys Leu Ser Cys Ala Ala Ser Gly Phe Asp Phe Ser Arg Tyr Trp Met Ser Trp Val Arg Gln Ala Pro Gly Lys Gly Leu Glu Trp Ile Gly Glu Ile Asn Pro Asp Ser Ser Thr Ile Asn Tyr Thr Pro Ser Leu Lys Asp Lys Phe Ile Ile Ser Arg Asp Asn Ala Lys Asn Thr Leu Tyr Leu Gln Met Ser Lys Val Arg Ser Glu Asp Thr Ala Leu Tyr Tyr Cys Ala Arg Pro Asp Gly Asn Tyr Trp Tyr Phe Asp Val Trp Gly Ala Gly Thr Thr Val Thr Val Ser Ser |
| 2 | Luc63 light chain variable region | Asp Ile Val Met Thr Gln Ser His Lys Phe Met Ser Thr Ser Val Gly Asp Arg Val Ser Ile Thr Cys Lys Ala Ser Gln Asp Val Gly Ile Ala Val Ala Trp Tyr Gln Gln Lys Pro Gly Gln Ser Pro Lys Leu Leu Ile Tyr Trp Ala Ser Thr Arg His Thr Gly Val Pro Asp Arg Phe Thr Gly Ser Gly Ser Gly Thr Asp Phe Thr Leu Thr Ile Ser Asn Val Gln Ser Glu Asp Leu Ala Asp Tyr Phe Cys Gln Gln Tyr Ser Ser Tyr Pro Tyr Thr Phe Gly Gly Gly Thr Lys Leu Glu Ile Lys |
| 3 | Luc63 heavy chain variable region CDR1 | RYWMS |
| 4 | Luc63 heavy chain variable region CDR2 | EINPDSSTINYTPSLKD |
| 5 | Luc63 heavy chain variable region CDR3 | PDGNYWYFDV |
| 6 | Luc63 light chain variable region CDR1 | KASQDVGIAVA |

| SEQ ID NO. | Description | Sequence |
|---|---|---|
| 7 | Luc63 light chain variable region CDR2 | WASTRHT |
| 8 | Luc63 light chain variable region CDR3 | QQYSSYPYT |
| 9 | HuLuc63 heavy chain variable region | Glu Val Gln Leu Val Glu Ser Gly Gly Gly Leu Val Gln Pro Gly Gly<br>1                                 5                           10                         15<br>Ser Leu Arg Leu Ser Cys Ala Ala Ser Gly Phe Asp Phe Ser Arg Tyr<br>                   20                         25                         30<br>Trp Met Ser Trp Val Arg Gln Ala Pro Gly Lys Gly Leu Glu Trp Ile<br>        35                            40                         45<br>Gly Glu Ile Asn Pro Asp Ser Ser Thr Ile Asn Tyr Ala Pro Ser Leu<br>    50                            55                         60<br>Lys Asp Lys Phe Ile Ile Ser Arg Asp Asn Ala Lys Asn Ser Leu Tyr<br>65                              70                        75                         80<br>Leu Gln Met Asn Ser Leu Arg Ala Glu Asp Thr Ala Val Tyr Tyr Cys<br>                   85                         90                         95<br>Ala Arg Pro Asp Gly Asn Tyr Trp Tyr Phe Asp Val Trp Gly Gln Gly<br>        100                         105                       110<br>Thr Leu Val Thr Val Ser Ser<br>    115 |
| 10 | HuLuc63 light chain variable region | Asp Ile Gln Met Thr Gln Ser Pro Ser Ser Leu Ser Ala Ser Val Gly<br>1                                 5                           10                         15<br>Asp Arg Val Thr Ile Thr Cys Lys Ala Ser Gln Asp Val Gly Ile Ala<br>                   20                         25                         30<br>Val Ala Trp Tyr Gln Gln Lys Pro Gly Lys Val Pro Lys Leu Leu Ile<br>        35                            40                         45<br>Tyr Trp Ala Ser Thr Arg His Thr Gly Val Pro Asp Arg Phe Ser Gly<br>    50                            55                         60<br>Ser Gly Ser Gly Thr Asp Phe Thr Leu Thr Ile Ser Ser Leu Gln Pro<br>65                              70                        75                         80<br>Glu Asp Val Ala Thr Tyr Tyr Cys Gln Gln Tyr Ser Ser Tyr Pro Tyr<br>                   85                         90                         95<br>Thr Phe Gly Gln Gly Thr Lys Val Glu Ile Lys<br>        100                         105 |
| 11 | HuLuc63 heavy chain variable region CDR1 | RYWMS |
| 12 | HuLuc63 heavy chain variable region CDR2 | EINPDSSTINYAPSLKD |
| 13 | HuLuc63 heavy chain variable region CDR3 | PDGNYWYFDV |
| 14 | HuLuc63 light chain variable region CDR1 | KASQDVGIAVA |
| 15 | HuLuc63 light chain variable region CDR2 | WASTRHT |
| 16 | HuLuc63 light chain variable region CDR3 | QQYSSYPYT |
| 17 | Luc90 heavy chain variable region | Gln Val Gln Leu Gln Gln Pro Gly Ala Glu Leu Val Arg Pro Gly Ala<br>1                                 5                           10                         15<br>Ser Val Lys Leu Ser Cys Lys Ala Ser Gly Tyr Ser Phe Thr Thr Tyr<br>                   20                         25                         30<br>Trp Met Asn Trp Val Lys Gln Arg Pro Gly Gln Gly Leu Glu Trp Ile<br>        35                            40                         45<br>Gly Met Ile His Pro Ser Asp Ser Glu Thr Arg Leu Asn Gln Lys Phe<br>    50                            55                         60<br>Lys Asp Lys Ala Thr Leu Thr Val Asp Lys Ser Ser Ser Thr Ala Tyr<br>65                              70                        75                         80<br>Met Gln Leu Ser Ser Pro Thr Ser Glu Asp Ser Ala Val Tyr Tyr Cys<br>                   85                         90                         95<br>Ala Arg Ser Thr Met Ile Ala Thr Arg Ala Met Asp Tyr Trp Gly Gln<br>        100                         105                       110<br>Gly Thr Ser Val Thr Val Ser Ser<br>        115                         120 |
| 18 | Luc90 light chain variable region | Asp Ile Val Met Thr Gln Ser Gln Lys Ser Met Ser Thr Ser Val Gly<br>1                                 5                           10                         15<br>Asp Arg Val Ser Ile Thr Cys Lys Ala Ser Gln Asp Val Ile Thr Gly |

-continued

| SEQ ID NO. | Description | Sequence |
|---|---|---|
| | | Val Ala Trp Tyr Gln Gln Lys Pro Gly Gln Ser Pro Lys Leu Leu Ile<br>                   20                         25                       30<br>Tyr Ser Ala Ser Tyr Arg Tyr Thr Gly Val Pro Asp Arg Phe Thr Gly<br> 35                            40                        45<br>Ser Gly Ser Gly Thr Asp Phe Thr Phe Thr Ile Ser Asn Val Gln Ala<br>65                         70                        75                   80<br>Glu Asp Leu Ala Val Tyr Tyr Cys Gln Gln His Tyr Ser Thr Pro Leu<br>                       85                         90                   95<br>Thr Phe Gly Ala Gly Thr Lys Leu Glu Leu Lys<br>           100                     105 |
| 19 | Luc90 heavy chain variable region CDR1 | TYWMN |
| 20 | Luc90 heavy chain variable region CDR2 | MIHPSDSETRLNQKFKD |
| 21 | Luc90 heavy chain variable region CDR3 | STMIATRAMDY |
| 22 | Luc90 light chain variable region CDR1 | KASQDVITGVA |
| 23 | Luc90 light chain variable region CDR2 | SASYRYT |
| 24 | Luc90 light chain variable region CDR3 | QQHYSTPLT |
| 25 | Luc34 heavy chain variable region | Gln Val Gln Leu Gln Gln Ser Gly Ala Glu Leu Ala Arg Pro Gly Ala<br>1                 5                         10                        15<br>Ser Val Lys Leu Ser Cys Lys Ala Ser Gly Tyr Thr Phe Thr Ser Tyr<br>                    20                         25                       30<br>Trp Met Gln Trp Val Lys Gln Arg Pro Gly Gln Gly Leu Glu Trp Ile<br> 35                            40                        45<br>Gly Ala Ile Tyr Pro Gly Asp Gly Asp Thr Arg Tyr Thr Gln Lys Phe<br>50                         55                        60<br>Lys Gly Lys Ala Thr Leu Thr Ala Asp Lys Ser Ser Ser Thr Ala Tyr<br>65                       70                        75                   80<br>Met Gln Leu Ser Ser Leu Ala Ser Glu Asp Ser Ala Val Tyr Tyr Cys<br>                       85                         90                   95<br>Ala Arg Gly Lys Val Tyr Tyr Gly Ser Asn Pro Phe Ala Tyr Trp Gly<br>                 100                     105                   110<br>Gln Gly Thr Leu Val Thr Val Ser Ala<br>           115                     120 |
| 26 | Luc34 light chain variable region | Asp Ile Gln Met Thr Gln Ser Ser Ser Tyr Leu Ser Val Ser Leu Gly<br>1                 5                         10                        15<br>Gly Arg Val Thr Ile Thr Cys Lys Ala Ser Asp His Ile Asn Asn Trp<br>                    20                         25                       30<br>Leu Ala Trp Tyr Gln Gln Lys Pro Gly Asn Ala Pro Arg Leu Leu Ile<br> 35                            40                        45<br>Ser Gly Ala Thr Ser Leu Glu Thr Gly Val Pro Ser Arg Phe Ser Gly<br>50                         55                        60<br>Ser Gly Ser Gly Lys Asp Tyr Thr Leu Ser Ile Thr Ser Leu Gln Thr<br>65                         70                        75                   80<br>Glu Asp Val Ala Thr Tyr Tyr Cys Gln Gln Tyr Trp Ser Thr Pro Trp<br>                       85                         90                   95<br>Thr Phe Gly Gly Gly Thr Lys Leu Glu Ile Lys<br>           100                     105 |
| 27 | Luc34 heavy chain variable region CDR1 | SYWMQ |
| 28 | Luc34 heavy chain variable region CDR2 | AIYPGDGDTRYTQKFKG |
| 29 | Luc34 heavy chain variable region CDR3 | GKVYYGSNPFAY |
| 30 | Luc34 light chain variable region CDR1 | KASDHINNWLA |
| 31 | Luc34 light chain variable region CDR2 | GATSLET |

-continued

| SEQ ID NO. | Description | Sequence |
|---|---|---|
| 32 | Luc34 light chain variable region CDR3 | QQYWSTPWT |
| 33 | LucX.2 heavy chain variable region | Gln Val Gln Leu Gln Gln Ser Gly Pro Glu Leu Val Lys Pro Gly Ala<br>1               5                   10                  15<br>Ser Val Lys Ile Ser Cys Lys Ala Ser Gly Tyr Ala Phe Ser Ser Ser<br>           20                  25                  30<br>Trp Met Asn Trp Val Lys Gln Arg Pro Gly Gln Gly Leu Glu Trp Ile<br>       35                  40                  45<br>Gly Arg Ile Tyr Pro Gly Asp Gly Asp Thr Lys Tyr Asn Gly Lys Phe<br>   50                  55                  60<br>Lys Gly Lys Ala Thr Leu Thr Ala Asp Lys Ser Ser Ser Thr Ala Tyr<br>65                  70                  75                  80<br>Met Gln Leu Ser Ser Leu Thr Ser Val Asp Ser Ala Val Tyr Phe Cys<br>           85                  90                  95<br>Ala Arg Ser Thr Met Ile Ala Thr Gly Ala Met Asp Tyr Trp Gly Gln<br>       100                 105                 110<br>Gly Thr Ser Val Thr Val Ser Ser<br>   115                 120 |
| 34 | LucX.2 light chain variable region | Asp Ile Val Met Thr Gln Ser His Lys Phe Met Ser Thr Ser Val Gly<br>1               5                   10                  15<br>Asp Arg Val Ser Ile Thr Cys Lys Ala Ser Gln Asp Val Ser Thr Ala<br>           20                  25                  30<br>Val Ala Trp Tyr Gln Gln Lys Pro Gly Gln Ser Pro Lys Leu Leu Ile<br>       35                  40                  45<br>Tyr Ser Ala Ser Tyr Arg Tyr Thr Gly Val Pro Asp Arg Phe Thr Gly<br>   50                  55                  60<br>Ser Gly Ser Gly Thr Asp Phe Thr Phe Thr Ile Ser Ser Val Gln Ala<br>65                  70                  75                  80<br>Glu Asp Leu Ala Val Tyr Tyr Cys Gln Gln His Tyr Ser Thr Pro Pro<br>           85                  90                  95<br>Tyr Thr Phe Gly Gly Gly Thr Lys Leu Glu Ile Lys<br>       100                 105 |
| 35 | LucX.2 heavy chain variable region CDR1 | SSWMN |
| 36 | LucX.2 heavy chain variable region CDR2 | RIYPGDGDTKYNGKFKG |
| 37 | LucX.2 heavy chain variable region CDR3 | STMIATGAMDY |
| 38 | LucX.2 light chain variable region CDR1 | KASQDVSTAVA |
| 39 | LucX.2 light chain variable region CDR2 | SASYRYT |
| 40 | LucX.2 light chain variable region CDR3 | QQHYSTPPYT |

Light and heavy chain variable region sequences (in three-letter code) and CDR sequences (in single letter code) of anti-CS1 antibodies useful for treatment of rare lymphomas.

In certain embodiments, anti-CS1 antibodies useful in the methods disclosed herein compete with Luc63 or Luc90 for binding to CS1. The ability to compete for binding to CS1 can be tested using a competition assay. In one example of a competition assay, CS1 is adhered onto a solid surface, e.g., a microwell plate, by contacting the plate with a solution of CS1 (e.g., at a concentration of 5 µg/ml in PBS over night at 4° C.). The plate is washed and blocked (e.g., in TBS buffer with 5 mM $CaCl_2$ and 2% BSA). A solution of fluorescently labeled Luc63 or Luc90 (the "reference" antibody) (e.g., at a concentration of 1 µg/ml, 2 µg/ml, or 5 µg/ml) is added to the plate and plates are incubated for 2 hours. The plate is washed, the competing anti-CS1 antibody (the "test" antibody) is added (e.g., at a concentration of 3 µg/ml, 10 µg/ml, 20 µg/ml, 50 µg/ml or 100 µg/ml), and the plates incubated for 1 hour. The assay can be performed in parallel at different concentrations of competing antibody. Plates are washed and the mean fluorescence intensity ("MFI") is measured as compared to control plates (which were not incubated with a test antibody, e.g., were incubated with an isotype control antibody). Variations on this neutralizing assay can also be used to test competition between Luc63 or Luc90 and another anti-CS1 antibody. For example, in certain aspects, the anti-CS1 antibody is used as a reference antibody and Luc63 or Luc90 is used as a test antibody. Additionally, instead of soluble CS1 membrane-bound CS1 can be used, for example recombinantly expressed on cells (preferably mammalian cells, e.g., COS cells) in culture. Generally, about $10^4$ to $10^6$ transfectants, and, in a specific embodiment, about $10^5$ transfectants, are used. Other formats for competition assays are known in the art and can be employed. The hybridoma cell line producing the antibody Luc90 has been deposited with the American Type Culture Collection (ATCC) at P.O. Box 1549, Manassas, Va. 20108, as accession number PTA-5091.

The deposit of this hybridoma cell line was received by the ATCC on Mar. 26, 2003. The hybridoma cell line Luc63 has also been deposited with the ATCC at the address listed above, as accession number PTA-5950. The deposit of the Luc63 antibody was received by the ATCC on May 6, 2004.

In various embodiments, an anti-CS1 antibody useful to treat a rare lymphoma reduces the MFI of labeled Luc63 or Luc90 by at least 40%, by at least 50%, by at least 60%, by at least 70%, by at least 80%, by at least 90%, or by a percentage ranging between any two of the foregoing values (e.g., an anti-CS1 antibody reduces the MFI of labeled Luc63 or luc90 by 50% to 70%) when the anti-CS1 antibody is used at a concentration of 3 µg/ml, 10 µg/ml, 20 µg/ml, 50 µg/ml, 100 µg/ml, or at a concentration ranging between any two of the foregoing values (e.g., at a concentration ranging from 20 µg/ml to 50 µg/ml).

In other embodiments, Luc63 or Luc90 reduces the MFI of a labeled anti-CS1 antibody useful in the methods disclosed herein by at least 40%, by at least 50%, by at least 60%, by at least 70%, by at least 80%, by at least 90%, or by a percentage ranging between any two of the foregoing values (e.g., Luc63 or Luc90 reduces the MFI of a labeled an anti-CS1 antibody by 50% to 70%) when Luc63 or Luc90 is used at a concentration of 3 µg/ml, 10 µg/ml, 20 µg/ml, 50 µg/ml, 100 µg/ml, or at a concentration ranging between any two of the foregoing values (e.g., at a concentration ranging from 10 µg/ml to 50 µg/ml).

Anti-CS1 antibodies useful in the present methods include antibodies that induce antibody-dependent cytotoxicity (ADCC) of CS1-expressing cells. The ADCC of an anti-CS1 antibody can be improved by using antibodies that have low levels of or lack fucose. Antibodies lacking fucose have been correlated with enhanced ADCC (antibody-dependent cellular cytotoxicity) activity, especially at low doses of antibody (Shields et al., 2002, J. Biol. Chem. 277:26733-26740; Shinkawa et al., 2003, J. Biol. Chem. 278:3466). Methods of preparing fucose-less antibodies include growth in rat myeloma YB2/0 cells (ATCC CRL 1662). YB2/0 cells express low levels of FUT8 mRNA, which encodes an enzyme (.alpha. 1,6-fucosyltransferase) necessary for fucosylation of polypeptides. Alternative methods for increasing ADDC activity include mutations in the Fc portion of a CS1 antibody, particularly mutations which increase antibody affinity for an FcγR receptor. A correlation between increased FcγR binding with mutated Fc has been demonstrated using targeted cytoxicity cell-based assays (Shields et al., 2001, J. Biol. Chem. 276:6591-6604; Presta et al., 2002, Biochem Soc. Trans. 30:487-490). Methods for increasing ADCC activity through specific Fc region mutations include the Fc variants comprising at least one amino acid substitution at a position selected from the group consisting of: 234, 235, 239, 240, 241, 243, 244, 245, 247, 262, 263, 264, 265, 266, 267, 269, 296, 297, 298, 299, 313, 325, 327, 328, 329, 330 and 332, wherein the numbering of the residues in the Fc region is that of the EU index as in Kabat (Kabat et al., Sequences of Proteins of Immunological Interest (National Institute of Health, Bethesda, Md. 1987). In certain specific embodiments, said Fc variants comprise at least one substitution selected from the group consisting of L234D, L234E, L234N, L234Q, L234T, L234H, L234Y, L234I, L234V, L234F, L235D, L235S, L235N, L235Q, L235T, L235H, L235Y, L235I, L235V, L235F, S239D, S239E, S239N, S239Q, S239F, S239T, S239H, S239Y, V240I, V240A, V240T, V240M, F241W, F241L, F241Y, F241E, F241R, F243W, F243L, F243Y, F243R, F243Q, P244H, P245A, P247V, P247G, V262I, V262A, V262T, V262E, V263I, V263A, V263T, V263M, V264L, V264I, V264W, V264T, V264R, V264F, V264M, V264Y, V264E, D265G, D265N, D265Q, D265Y, D265F, D265V, D265I, D265L, D265H, D265T, V266I, V266A, V266T, V266M, S267Q, S267L, E269H, E269Y, E269F, E269R, Y296E, Y296Q, Y296D, Y296N, Y296S, Y296T, Y296L, Y296I, Y296H, N297S, N297D, N297E, A298H, T299I, T299L, T299A, T299S, T299V, T299H, T299F, T299E, W313F, N325Q, N325L, N325I, N325D, N325E, N325A, N325T, N325V, N325H, A327N, A327L, L328M, L328D, L328E, L328N, L328Q, L328F, L328I, L328V, L328T, L328H, L328A, P329F, A330L, A330Y, A330V, A330I, A330F, A330R, A330H, I332D, I332E, I332N, I332Q, I332T, I332H, I332Y and I332A, wherein the numbering of the residues in the Fc region is that of the EU index as in Kabat. Fc variants can also be selected from the group consisting of V264L, V264I, F241W, F241L, F243W, F243L, F241L/F243L/V262I/V264I, F241W/ F243W, F241W/F243W/V262A/V264A, F241L/V262I, F243L/V264I, F243L/V262I/V264W, F241Y/F243Y/ V262T/V264T, F241E/F243R/V262E/V264R, F241E/ F243Q/V262T/V264E, F241R/F243Q/V262T/V264R, F241E/F243Y/V262T/V264R, L328M, L328E, L328F, I332E, L3238M/I332E, P244H, P245A, P247V, W313F, P244H/P245A/P247V, P247G, V264I/I332E, F241E/F243R/ V262E/V264R/I332E, F241E/F243Q/V262T/264E/I332E, F241R/F243Q/V262T/V264R/I332E, F241E/F243Y/ V262T/V264R/I332E, S298A/I332E, S239E/I332E, S239Q/ I332E, S239E, D265G, D265N, S239E/D265G, S239E/ D265N, S239E/D265Q, Y296E, Y296Q, T299I, A327N, S267Q/A327S, S267L/A327S, A327L, P329F, A330L, A330Y, I332D, N297S, N297D, N297S/I332E, N297D/ I332E, N297E/I332E, D265Y/N297D/I332E, D265Y/ N297D/T299L/I332E, D265F/N297E/I332E, L328I/I332E, L328Q/I332E, I332N, I332Q, V264T, V264F, V240I, V263I, V266I, T299A, T299S, T299V, N325Q, N325L, N325I, S239D, S239N, S239F, S239D/I332D, S239D/I332E, S239D/I332N, S239D/I332Q, S239E/I332D, S239E/I332N, S239E/I332Q, S239N/I332D, S239N/I332E, S239N/I332N, S239N/I332Q, S239Q/I332D, S239Q/I332N, S239Q/I332Q, Y296D, Y296N, F241Y/F243Y/V262T/V264T/N297D/ I332E, A330Y/I332E, V264I/A330Y/I332E, A330L/I332E, V264I/A330L/I332E, L234D, L234E, L234N, L234Q, L234T, L234H, L234Y, L234I, L234V, L234F, L235D, L235S, L235N, L235Q, L235T, L235H, L235Y, L235I, L235V, L235F, S239T, S239H, S239Y, V240A, V240T, V240M, V263A, V263T, V263M, V264M, V264Y, V266A, V266T, V266M, E269H, E269Y, E269F, E269R, Y296S, Y296T, Y296L, Y296I, A298H, T299H, A330V, A330I, A330F, A330R, A330H, N325D, N325E, N325A, N325T, N325V, N325H, L328D/I332E, L328E/I332E, L328N/ I332E, L328Q/I332E, L328V/I332E, L328T/I332E, L328H/ I332E, L328I/I332E, L328A, I332T, I332H, I332Y, I332A, S239E/V264I/I332E, S239Q/V264I/I332E, S239E/V264I/ A330Y/I332E, S239E/V264I/S298A/A330Y/I332E, S239D/N297D/I332E, S239E/N297D/I332E, S239D/ D265V/N297D/I332E, S239D/D265I/N297D/I332E, S239D/D265L/N297D/I332E, S239D/D265F/N297D/ I332E, S239D/D265Y/N297D/I332E, S239D/D265H/ N297D/I332E, S239D/D265T/N297D/I332E, V264E/ N297D/I332E, Y296D/N297D/I332E, Y296E/N297D/ I332E, Y296N/N297D/I332E, Y296Q/N297D/I332E, Y296H/N297D/I332E, Y296T/N297D/I332E, N297D/ T299V/I332E, N297D/T299I/I332E, N297D/T299L/I332E, N297D/T299F/I332E, N297D/T299H/I332E, N297D/ T299E/I332E, N297D/A330Y/I332E, N297D/S298A/ A330Y/I332E, S239D/A330Y/I332E, S239N/A330Y/ I332E, S239D/A330L/I332E, S239N/A330L/I332E, V264I/ S298A/I332E, S239D/S298A/I332E, S239N/S298A/I332E, S239D/V264I/I332E, S239D/V264I/S298A/I332E, AND S239D/264I/A330L/I332E, wherein the numbering of the residues in the Fc region is that of the EU index as in Kabat. See also PCT WO 2004/029207, Apr. 8, 2004, incorporated by reference herein.

Antibody-associated ADCC activity can be monitored and quantified through measurement of lactate dehydrogenase (LDH) release in the culture supernatant of CS1-expressing cells, which is rapidly released upon damage to the plasma membrane. The CS1-expressing cells are in certain embodiments lymphoma cells, for example T-cell, NK-cell, or NK-T cell lymphoma cells. In various embodiments, the antibodies induce at least 10%, 20%, 30%, 40%, 50%, 60%, or 80% cytotoxicity of the target cells. An example of an ADCC assay that can be used to measure ADCC of an anti-CS1 antibody is that of Tai et al., 2008, Blood 112:1329-1337.

Also encompassed by the present disclosure is the use of anti-CS1 scFv molecules. The term "scFv" refers to a single chain Fv antibody in which the variable domains of the heavy chain and the light chain from a traditional antibody have been joined to form one chain.

References to "VH" refer to the variable region of an immunoglobulin heavy chain of an antibody, including the heavy chain of an Fv, scFv, or Fab. References to "VL" refer to the variable region of an immunoglobulin light chain, including the light chain of an Fv, scFv, dsFv or Fab. Antibodies (Abs) and immunoglobulins (Igs) are glycoproteins having the same structural characteristics. While antibodies exhibit binding specificity to a specific target, immunoglobulins include both antibodies and other antibody-like molecules which lack target specificity. Native antibodies and immunoglobulins are usually heterotetrameric glycoproteins of about 150,000 daltons, composed of two identical light (L) chains and two identical heavy (H) chains. Each heavy chain has at one end a variable domain (VH) followed by a number of constant domains. Each light chain has a variable domain at one end (VL) and a constant domain at its other end.

Complementary Determining Regions ("CDRs") refers to the hypervariable regions in the light chain and the heavy chain variable domains. The more highly conserved portions of variable domains are called the framework regions ("FR"). The amino acid position/boundary delineating a hypervariable region of an antibody can vary, depending on the context and the various definitions known in the art. Some positions within a variable domain can be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The variable domains of native heavy and light chains each comprise four FR regions, largely by adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the target binding site of antibodies (See Kabat et al., Sequences of Proteins of Immunological Interest (National Institute of Health, Bethesda, Md. 1987). As used herein, numbering of immunoglobulin amino acid residues is done according to the immunoglobulin amino acid residue numbering system of Kabat et al., unless otherwise indicated.

The term "antibody fragment" refers to a portion of a full-length antibody, generally the target binding or variable region. Examples of antibody fragments include Fab, Fab', F(ab')2 and Fv fragments. An "Fv" fragment is the minimum antibody fragment which contains a complete target recognition and binding site. This region consists of a dimer of one heavy and one light chain variable domain in a tight, non-covalent association (VH-VL dimer). It is in this configuration that the three CDRs of each variable domain interact to define a target binding site on the surface of the VH-VL dimer. Collectively, the six CDRs confer target binding specificity to the antibody. However, even a single variable domain (or half of an Fv comprising only three CDRs specific for a target) has the ability to recognize and bind target, although at a lower affinity than the entire binding site. "Single-chain Fv" or "sFv" antibody fragments comprise the VH and VL domains of an antibody, wherein these domains are present in a single polypeptide chain. Generally, the Fv polypeptide further comprises a polypeptide linker between the VH and VL domains which enables the sFv to form the desired structure for target binding.

The Fab fragment contains the constant domain of the light chain and the first constant domain (CH1) of the heavy chain. Fab' fragments differ from Fab fragments by the addition of a few residues at the carboxyl terminus of the heavy chain $CH_1$ domain including one or more cysteines from the antibody hinge region. F(ab') fragments are produced by cleavage of the disulfide bond at the hinge cysteines of the $F(ab')_2$ pepsin digestion product. Additional chemical couplings of antibody fragments are known to those of ordinary skill in the art.

In some embodiments, the anti-CS1 antibodies are monoclonal antibodies. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Monoclonal antibodies can be prepared using a wide variety of techniques known in the art including the use of hybridoma, recombinant, and phage display technologies, or a combination thereof. In other embodiments, including in vivo use of the anti-CS1 antibodies in humans and in vitro detection assays, chimeric, primatized, humanized, or human antibodies can be used.

In some embodiments, the anti-CS1 antibodies are chimeric antibodies. The term "chimeric" antibody as used herein refers to an antibody having variable sequences derived from a non-human immunoglobulins, such as rat or mouse antibody, and human immunoglobulins constant regions, typically chosen from a human immunoglobulin template. Methods for producing chimeric antibodies are known in the art. See, e.g., Morrison, 1985, Science 229 (4719):1202-7; Oi et al., 1986, BioTechniques 4:214-221; Gillies et al., 1985, J. Immunol. Methods 125:191-202; U.S. Pat. Nos. 5,807,715; 4,816,567; and 4,816397, which are incorporated herein by reference in their entireties.

In some embodiments, the anti-CS1 antibodies are humanized antibodies. "Humanized" forms of non-human (e.g., murine) antibodies are chimeric immunoglobulins, immunoglobulin chains or fragments thereof (such as Fv, Fab, Fab', $F(ab')_2$ or other target-binding subsequences of antibodies) which contain minimal sequences derived from non-human immunoglobulin. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody can also comprise at least a portion of an immunoglobulin constant region (Fc), typically that of a human immunoglobulin template chosen. Humanization is a technique for making a chimeric antibody in which one or more amino acids or portions of the human variable domain have been substituted by the corresponding sequence from a non-human species. Humanized antibodies are antibody molecules generated in a non-human species that bind the desired antigen having one or more complementarity determining regions (CDRs) from the non-human species and framework (FR) regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., Riechmann et al., 1988, Nature 332:323-7 and Queen et al., U.S. Pat. Nos. 5,530,101; 5,585,089; 5,693,761; 5,693,762; and 6,180,370 (each of which is incorporated by reference in its entirety). Antibodies can be humanized using a variety of techniques known in the art including, for example, CDR-grafting (EP239400; PCT publication WO 91/09967; U.S. Pat. Nos. 5,225,539; 5,530, 101 and 5,585,089), veneering or resurfacing (EP592106; EP519596; Padlan, 1991, Mol. Immunol., 28:489-498; Studnicka et al., 1994, Prot. Eng. 7:805-814; Roguska et al., 1994, Proc. Natl. Acad. Sci. 91:969-973, and chain shuffling (U.S. Pat. No. 5,565,332), all of which are hereby incorporated by reference in their entireties.

In some embodiments, humanized antibodies are prepared as described in Queen et al., U.S. Pat. Nos. 5,530,101; 5,585, 089; 5,693,761; 5,693,762; and 6,180,370 (each of which is incorporated by reference in its entirety).

In some embodiments, the anti-CS1 antibodies are human antibodies. Completely "human" anti-CS1 antibodies can be desirable for therapeutic treatment of human patients. As used herein, "human antibodies" include antibodies having the amino acid sequence of a human immunoglobulin and include antibodies isolated from human immunoglobulin libraries or from animals transgenic for one or more human immunoglobulin and that do not express endogenous immunoglobulins. Human antibodies can be made by a variety of methods known in the art including phage display methods described above using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety. Human antibodies can also be produced using transgenic mice which are incapable of expressing functional endogenous immunoglobulins, but which can express human immunoglobulin genes. See, e.g., PCT publications WO 98/24893; WO 92/01047; WO 96/34096; WO 96/33735; U.S. Pat. Nos. 5,413,923; 5,625, 126; 5,633,425; 5,569,825; 5,661,016; 5,545,806; 5,814,318; 5,885,793; 5,916,771; and 5,939,598, which are incorporated by reference herein in their entireties. In addition, companies such as Abgenix (Fremont, Calif.) (now part of Amgen) and Medarex (Princeton, N.J.) can be engaged to provide human antibodies directed against a selected antigen using technology similar to that described above. Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al., 1988, Biotechnology 12:899-903).

In some embodiments, the anti-CS1 antibodies are primatized antibodies. The term "primatized antibody" refers to an antibody comprising monkey variable regions and human constant regions. Methods for producing primatized antibodies are known in the art. See e.g., U.S. Pat. Nos. 5,658,570; 5,681,722; and 5,693,780, which are incorporated herein by reference in their entireties.

In some embodiments, the anti-CS1 antibodies are bispecific antibodies. Bispecific antibodies are monoclonal, preferably human or humanized, antibodies that have binding specificities for at least two different antigens. In the bispecific antibodies useful in the present methods, one of the binding specificities can be directed towards CS1, the other can be for any other antigen, and preferably for a cell-surface protein, receptor, receptor subunit, tissue-specific antigen, virally derived protein, virally encoded envelope protein, bacterially derived protein, or bacterial surface protein, etc.

In some embodiments, the anti-CS1 antibodies are derivatized antibodies. For example, but not by way of limitation, the derivatized antibodies that have been modified, e.g., by glycosylation, acetylation, pegylation, phosphorylation, amidation, derivatization by known protecting/blocking groups, proteolytic cleavage, linkage to a cellular ligand or other protein (see Section 5.2 for a discussion of antibody conjugates), etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

In some embodiments, the anti-CS1 antibodies or fragments thereof can be antibodies or antibody fragments whose sequence has been modified to reduce at least one constant region-mediated biological effector function relative to the corresponding wild type sequence. To modify an anti-CS1 antibody such that it exhibits reduced binding to the Fc receptor, the immunoglobulin constant region segment of the antibody can be mutated at particular regions necessary for Fc receptor (FcR) interactions (See e.g., Canfield and Morrison, 1991, J. Exp. Med. 173:1483-1491; and Lund et al., 1991, J. Immunol. 147:2657-2662). Reduction in FcR binding ability of the antibody can also reduce other effector functions which rely on FcR interactions, such as opsonization and phagocytosis and antigen-dependent cellular cytotoxicity.

In yet other aspects, the anti-CS1 antibodies or fragments thereof can be antibodies or antibody fragments that have been modified to acquire at least one constant region-mediated biological effector function relative to an unmodified antibody. To modify an anti-CS1 antibody such that it exhibits increased binding to the Fcγ receptor (FcγR), the immunoglobulin constant region segment of the antibody can be mutated to enhance FcγR interactions (See, e.g., US 2006/0134709 A1). Enhancement of FcγR binding can increase antigen-dependent cellular cytotoxicity of an anti-CS1 antibody. In specific embodiments, an anti-CS1 antibody has a constant region that binds FcγRIIA, FcγRIIB and/or FcγRIIIA with greater affinity than the corresponding wild type constant region.

In yet another aspects, the anti-CS1 antibodies or fragments thereof can be antibodies or antibody fragments that have been modified to increase or reduce their binding affinities to the fetal Fc receptor, FcRn. To alter the binding affinity to FcRn, the immunoglobulin constant region segment of the antibody can be mutated at particular regions necessary for FcRn interactions (See e.g., WO 2005/123780). Increasing the binding affinity to FcRn should increase the antibody's serum half-life, and reducing the binding affinity to FcRn should conversely reduce the antibody's serum half-life. In particular embodiments, the anti-CS1 antibody is of the IgG class in which at least one of amino acid residues 250, 314, and 428 of the heavy chain constant region is substituted with an amino acid residue different from that present in the unmodified antibody. The antibodies of IgG class include antibodies of $IgG_1$, $IgG_2$, $IgG_3$, and $IgG_4$. The substitution can be made at position 250, 314, or 428 alone, or in any combinations thereof, such as at positions 250 and 428, or at positions 250 and 314, or at positions 314 and 428, or at positions 250, 314, and 428, with positions 250 and 428 as a preferred combination. For each position, the substituting amino acid can be any amino acid residue different from that present in that position of the unmodified antibody. For position 250, the substituting amino acid residue can be any amino acid residue other than threonine, including, but not limited to, alanine, cysteine, aspartic acid, glutamic acid, phenylalanine, glycine, histidine, isoleucine, lysine, leucine, methionine, asparagine, proline, glutamine, arginine, serine, valine, tryptophan, or tyrosine. For position 314, the substituting amino acid residue can be any amino acid residue other than leucine, including, but not limited to, alanine, cysteine, aspartic acid, glutamic acid, phenylalanine, glycine, histidine, isoleucine, lysine, methionine, asparagine, proline, glutamine, arginine, serine, threonine, valine, tryptophan, or tyrosine. For position 428, the substituting amino acid residues can be any amino acid residue other than methionine, including, but not limited to, alanine, cysteine, aspartic acid, glutamic acid, phenylalanine, glycine, histidine, isoleucine, lysine, leucine, asparagine, proline, glutamine, arginine, serine, threonine, valine, tryptophan, or tyrosine. Specific combinations of suitable amino acid substitutions are identified in Table 1 of WO 2005/123780, which table is incorporated by reference herein in its entirety. See also, Hinton et al., U.S. Pat. Nos. 7,217,797, 7,361,740, 7,365,168, and 7,217,798, which are incorporated herein by reference in their entireties.

In yet other aspects, an anti-CS1 antibody has one or more amino acids inserted into one or more of its hypervariable region, for example as described in US 2007/0280931.

5.2 Antibody Conjugates

In some embodiments, the anti-CS1 antibodies are antibody conjugates that are modified, e.g., by the covalent attachment of any type of molecule to the antibody, such that covalent attachment does not interfere with binding to CS1.

For example, in some embodiments an anti-CS1 antibody can be conjugated to an effector moiety or a label. The term "effector moiety" as used herein includes, for example, antineoplastic agents, drugs, toxins, biologically active proteins, for example enzymes, other antibody or antibody fragments, synthetic or naturally occurring polymers, nucleic acids (e.g., DNA and RNA), radionuclides, particularly radioiodide, radioisotopes, chelated metals, nanoparticles and reporter groups such as fluorescent compounds or compounds which can be detected by NMR or ESR spectroscopy.

By way of another example, anti-CS1 antibodies can be conjugated to an effector moiety, such as a cytotoxic agent, a radionuclide or drug moiety to modify a given biological response. The effector moiety can be a protein or polypeptide, such as, for example and without limitation, a toxin (such as abrin, ricin A, *Pseudomonas* exotoxin, or *Diphtheria* toxin), a signaling molecule (such as α-interferon, β-interferon, nerve growth factor, platelet derived growth factor or tissue plasminogen activator), a thrombotic agent or an anti-angiogenic agent (e.g., angiostatin or endostatin) or a biological response modifier such as a cytokine or growth factor (e.g., interleukin-1 (IL-1), interleukin-2 (IL-2), interleukin-6 (IL-6), granulocyte macrophage colony stimulating factor (GM-CSF), granulocyte colony stimulating factor (G-CSF), or nerve growth factor (NGF)).

In another example the effector moieties can be cytotoxins or cytotoxic agents. Examples of cytotoxins and cytotoxic agents include taxol, cytochalasin B, gramicidin D, ethidium bromide, emetine, mitomycin, etoposide, tenoposide, vincristine, vinblastine, colchicin, doxorubicin, daunorabicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector moieties also include, but are not limited to, anti-metabolites (e.g. methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C5 and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, anthramycin (AMC), calicheamicins or duocarmycins), and anti-mitotic agents (e.g., vincristine and vinblastine).

Other effector moieties can include radionuclides such as, but not limited to, $In^{111}$ and $Y^{90}$, $Lu^{177}$, $Bismuth^{213}$, $Californium^{252}$, $Iridium^{192}$ and $Tungsten^{188}/Rhenium^{188}$ and drugs such as, but not limited to, alkylphosphocholines, topoisomerase I inhibitors, taxoids and suramin.

Techniques for conjugating such effector moieties to antibodies are well known in the art (See, e.g., Hellstrom et al., Controlled Drug Delivery, 2nd Ed., at pp. 623-53 (Robinson et al., eds., 1987)); Thorpe et al., 1982, Immunol. Rev. 62:119-58 and Dubowchik et al., 1999, Pharmacology and Therapeutics 83:67-123).

In one example, the antibody or fragment thereof is fused via a covalent bond (e.g., a peptide bond), at optionally the N-terminus or the C-terminus, to an amino acid sequence of another protein (or portion thereof; preferably at least a 10, 20 or 50 amino acid portion of the protein). Preferably the antibody, or fragment thereof, is linked to the other protein at the N-terminus of the constant domain of the antibody. Recombinant DNA procedures can be used to create such fusions, for example as described in WO 86/01533 and EP0392745. In another example the effector molecule can increase half-life in vivo, and/or enhance the delivery of an antibody across an epithelial barrier to the immune system. Examples of suitable effector molecules of this type include polymers, albumin, albumin binding proteins or albumin binding compounds such as those described in WO 2005/117984.

In some embodiments, anti-CS1 antibodies can be attached to poly(ethyleneglycol) (PEG) moieties. For example, if the antibody is an antibody fragment, the PEG moieties can be attached through any available amino acid side-chain or terminal amino acid functional group located in the antibody fragment, for example any free amino, imino, thiol, hydroxyl or carboxyl group. Such amino acids can occur naturally in the antibody fragment or can be engineered into the fragment using recombinant DNA methods. See for example U.S. Pat. No. 5,219,996. Multiple sites can be used to attach two or more PEG molecules. Preferably PEG moieties are covalently linked through a thiol group of at least one cysteine residue located in the antibody fragment. Where a thiol group is used as the point of attachment, appropriately activated effector moieties, for example thiol selective derivatives such as maleimides and cysteine derivatives, can be used.

In another example, an anti-CS1 antibody conjugate is a modified Fab' fragment which is PEGylated, i.e., has PEG (poly(ethyleneglycol)) covalently attached thereto, e.g., according to the method disclosed in EP0948544. See also Poly(ethyleneglycol) Chemistry, Biotechnical and Biomedical Applications, (J. Milton Harris (ed.), Plenum Press, New York, 1992); Poly(ethyleneglycol) Chemistry and Biological Applications, (J. Milton Harris and S. Zalipsky, eds., American Chemical Society, Washington D.C., 1997); and Bioconjugation Protein Coupling Techniques for the Biomedical Sciences, (M. Aslam and A. Dent, eds., Grove Publishers, New York, 1998); and Chapman, 2002, Advanced Drug Delivery Reviews 54:531-545.

The word "label" when used herein refers to a detectable compound or composition which can be conjugated directly or indirectly to an anti-CS1 antibody. The label can itself be detectable (e.g., radioisotope labels or fluorescent labels) or, in the case of an enzymatic label, can catalyze chemical alteration of a substrate compound or composition which is detectable. Useful fluorescent moieties include, but are not limited to, fluorescein, fluorescein isothiocyanate, rhodamine, 5-dimethylamine-1-napthalenesulfonyl chloride, phycoerythrin and the like. Useful enzymatic labels include, but are not limited to, alkaline phosphatase, horseradish peroxidase, glucose oxidase and the like.

5.3 Therapeutic Methods, Pharmaceutical Compositions and Routes of Administration The CS1 antibodies described herein are useful for treating NK lymphomas, NK/T-cell lymphomas, and angioimmunoblastic T-cell lymphoma. Clinically, NK lymphomas and NK/T-cell lymphomas can be divided into nasal, non-nasal, and aggressive lymphoma/leukemia subtypes, all of which can benefit from treatment with an anti-CS1 antibody according to the methods described herein.

Treatment of a disease encompasses the treatment of patients already diagnosed as having any form of the disease at any clinical stage or manifestation; the delay of the onset or evolution or aggravation or deterioration of the symptoms or signs of the disease; and/or preventing and/or reducing the severity of the disease.

Prior to administering an anti-CS1 antibody for the treatment of lymphoma, the lymphoma can be tested for CS1 expression, for example by assaying a biopsy from the patient for CS1 RNA or protein. CS1 expression can be assayed on the biopsy sample (e.g., by immunohistochemistry) or on a nucleic acid or protein extract from the sample (e.g., using RT-PCR).

A "subject" or "patient" to whom an anti-CS1 antibody is administered can be a mammal, such as a non-primate (e.g., cow, pig, horse, cat, dog, rat, etc.) or a primate (e.g., monkey or human). In certain aspects, the human is a pediatric patient. In other aspects, the human is an adult patient.

Compositions comprising an anti-CS1 antibody and, optionally one or more additional therapeutic agents, such as the second therapeutic agents described in Section 5.4 below, are described herein. The compositions typically are supplied as part of a sterile, pharmaceutical composition that includes a pharmaceutically acceptable carrier. This composition can be in any suitable form (depending upon the desired method of administering it to a patient).

The anti-CS1 antibodies can be administered to a patient by a variety of routes such as orally, transdermally, subcutaneously, intranasally, intravenously, intramuscularly, intrathecally, topically or locally. The most suitable route for administration in any given case will depend on the particular antibody, the subject, and the nature and severity of the disease and the physical condition of the subject. Typically, an anti-CS1 antibody such as HuLuc63 will be administered intravenously.

In typical embodiments, an anti-CS1 antibody is present in a pharmaceutical composition at a concentration sufficient to permit intravenous administration at 0.5 mg/kg to 20 mg/kg. In some embodiments, the concentration of HuLuc63 suitable for use in the compositions and methods described herein includes, but is not limited to, 0.5 mg/kg, 0.75 mg/kg, 1 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, or a concentration ranging between any of the foregoing values, e.g., 1 mg/kg to 10 mg/kg, 5 mg/kg to 15 mg/kg, or 10 mg/kg to 18 mg/kg.

The effective dose of an anti-CS1 antibody can range from about 0.001 to about 750 mg/kg per single (e.g., bolus) administration, multiple administrations or continuous administration, or to achieve a serum concentration of 0.01-5000 µg/ml serum concentration per single (e.g., bolus) administration, multiple administrations or continuous administration, or any effective range or value therein depending on the condition being treated, the route of administration and the age, weight and condition of the subject. In certain embodiments, each dose can range from about 0.5 mg to about 50 mg per kilogram of body weight or from about 3 mg to about 30 mg per kilogram body weight. The antibody is can be formulated as an aqueous solution.

Pharmaceutical compositions can be conveniently presented in unit dose forms containing a predetermined amount of an anti-CS1 antibody per dose. Such a unit can contain 0.5 mg to 5 g, for example, but without limitation, 1 mg, 10 mg, 20 mg, 30 mg, 40 mg, 50 mg, 100 mg, 200 mg, 300 mg, 400 mg, 500 mg, 750 mg, 1000 mg, or any range between any two of the foregoing values, for example 10 mg to 1000 mg, 20 mg to 50 mg, or 30 mg to 300 mg. Pharmaceutically acceptable carriers can take a wide variety of forms depending, e.g., on the condition to be treated or route of administration.

Determination of the effective dosage, total number of doses, and length of treatment with an anti-CS1 antibody is well within the capabilities of those skilled in the art, and can be determined using a standard dose escalation study to identify the maximum tolerated dose (MTD) (see, e.g., Richardson et al., 2002, Blood, 100(9):3063-3067, the content of which is incorporated herein by reference).

Therapeutic formulations of the anti-CS1 antibodies suitable in the methods described herein can be prepared for storage as lyophilized formulations or aqueous solutions by mixing the antibody having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives must be nontoxic to the recipients at the dosages and concentrations employed.

Buffering agents help to maintain the pH in the range which approximates physiological conditions. They can present at concentration ranging from about 2 mM to about 50 mM. Suitable buffering agents include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives can be added to retard microbial growth, and can be added in amounts ranging from 0.2%-1% (w/v). Suitable preservatives include phenol, benzyl alcohol, meta-cresol, methyl paraben, propyl paraben, octadecyldimethyl-benzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions and include polhydric sugar alcohols, preferably trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers can be present in the range from 0.1 to 10,000 weights per part of weight active protein.

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic polyols, polyoxyethylene sorbitan monoethers (TWEEN®-20, TWEEN®-80, etc.). Non-ionic surfactants can be present in a range of about 0.05 mg/ml to about 1.0 mg/ml, or in a range of about 0.07 mg/ml to about 0.2 mg/ml.

Additional miscellaneous excipients include bulking agents (e.g., starch), chelating agents (e.g., EDTA), antioxidants (e.g., ascorbic acid, methionine, vitamin E), and cosolvents.

The formulation herein can also contain a second therapeutic agent in addition to an anti-CS1 antibody. Examples of suitable second therapeutic agents are provided in Section 5.4 below.

The dosing schedule can vary from once a month to daily depending on a number of clinical factors, including the type of disease, severity of disease, and the patient's sensitivity to the anti-CS1 antibody. In specific embodiments, an anti-CS1 antibody is administered daily, twice weekly, three times a week, every 5 days, every 10 days, every two weeks, every three weeks, every four weeks or once a month, or in any range between any two of the foregoing values, for example from every four weeks to every month, from every 10 days to every two weeks, or from two to three times a week, etc.

The dosage of an anti-CS1 antibody to be administered will vary according to the particular antibody, the subject, and the nature and severity of the disease, the physical condition of the subject, the therapeutic regimen (e.g., whether a second therapeutic agent is used), and the selected route of administration; the appropriate dosage can be readily determined by a person skilled in the art.

It will be recognized by one of skill in the art that the optimal quantity and spacing of individual dosages of an anti-CS1 antibody will be determined by the nature and extent of the condition being treated, the form, route and site of administration, and the age and condition of the particular subject being treated, and that a physician will ultimately determine appropriate dosages to be used. This dosage can be repeated as often as appropriate. If side effects develop the amount and/or frequency of the dosage can be altered or reduced, in accordance with normal clinical practice.

5.4 Combination Therapy

Described below are combinatorial methods in which the anti-CS1 antibodies can be utilized. The combinatorial methods involve the administration of at least two agents to a patient, the first of which is an anti-CS1 antibody and the second of which is a second therapeutic agent. The anti-CS1 antibody and the second therapeutic agent can be administered simultaneously, sequentially or separately.

Most nasal NK-cell lymphomas present with stage I/II disease, and frontline radiotherapy is the most important key to successful treatment. Many stage I/II patients treated with radiotherapy fail systemically, implying that concomitant chemotherapy may be needed. Chemotherapy is indicated for advanced nasal NK-cell lymphoma, and the non-nasal and aggressive subtypes. However, treatment results are generally unsatisfactory. High-dose chemotherapy with hematopoietic stem cell transplantation has been suggested to be beneficial to selected patients (Kwong et al., 2005, Leukemia 19:2186-94). An anti-CS1 antibody can be beneficially administered in combination with any therapeutic regimen entailing radiotherapy, chemotherapy, or other therapeutic agents. The combinatorial therapy methods described herein can result in a greater than additive effect, providing therapeutic benefits when monotherapy with the anti-CS1 antibody or second therapeutic agent is therapeutically effective.

An anti-CS1 antibody is typically administered approximately 0 to 60 days prior to or after the administration of a second therapeutic agent. In some embodiments, an anti-CS1 antibody is administered from about 30 minutes to about 1 hour prior to or after the administration of the second therapeutic agent, or from about 1 hour to about 2 hours prior to or after the administration of the second therapeutic agent, or from about 2 hours to about 4 hours prior to or after the administration of the second therapeutic agent, or from about 4 hours to about 6 hours prior to or after the administration of the second therapeutic agent, or from about 6 hours to about 8 hours prior to or after the administration of the second therapeutic agent, or from about 8 hours to about 16 hours prior to or after the administration of the second therapeutic agent, or from about 16 hours to 1 day prior to or after the administration of the second therapeutic agent, or from about 1 to 5 days prior to or after the administration of the second therapeutic agent, or from about 5 to 10 days prior to or after the administration of the second therapeutic agent, or from about 10 to 15 days prior to or after the administration of the second therapeutic agent, or from about 15 to 20 days prior to or after the administration of the second therapeutic agent, or from about 20 to 30 days prior to or after the administration of the second therapeutic agent, or from about 30 to 40 days prior to or after the administration of the second therapeutic agent, or from about 40 to 50 days prior to or after the administration of the second therapeutic agent, or from about 50 to 60 days prior to or after the administration of the second therapeutic agent. In this context, the term "about" with respect to any time period referenced supra may be construed to mean the numerical range stated less up to 20% at its lower end, to plus up to 20% at its upper end (e.g., a time period of "about 40 to 50 days" means a time period ranging from 32 to 60 days). In specific embodiment, the use of the term "about" in the context of a time period refers to the numerical range stated less 2%, 3%, 5%, 10%, or 15% at its lower end, plus up to 2%, 3%, 5%, 10%, or 15% at its upper end.

Thus, the anti-CS1 antibody and the second therapeutic agent can be administered concurrently, either simultaneously or successively. As used herein, the anti-CS1 antibody and the second therapeutic agent are said to be administered successively if they are administered to the patient on the same day, for example during the same patient visit. Successive administration can occur 1, 2, 3, 4, 5, 6, 7 or 8 hours apart. In contrast, the anti-CS1 antibody and the second therapeutic agent are said to be administered separately if they are administered to the patient on the different days, for example, the anti-CS1 antibody of the invention and the second therapeutic agent can be administered at a 1-day, 2-day or 3-day, one-week, 2-week or monthly intervals.

In the methods described herein, administration of the anti-CS1 antibody can precede or follow administration of the second therapeutic agent. As a non-limiting example, the anti-CS1 antibody and the second therapeutic agent can be administered concurrently for a period of time, followed by a second period of time in which the administration of the anti-CS1 antibody and the second therapeutic agent is alternated.

Because of the potentially synergistic effects of administering an anti-CS1 antibody and a second therapeutic agent, such agents can be administered in amounts that, if one or both of the agents is administered alone, is/are not therapeutically effective. For example, in various embodiments, the dosage of the anti-CS1 antibody and/or the dosage of the second therapeutic agent administered is about 10% to 90% of the generally accepted efficacious dose range for single therapy regimens. In some embodiments, about 10%, about 15%, about 25%, about 30%, about 40%, about 50%, about 60%, about 75%, or about 90% of the generally accepted efficacious dose range is used, or a dosage ranging between any of the foregoing values (e.g., 10% to 40%, 30% to 75%, or 60% to 90% of the of the generally accepted efficacious dose range) is used.

In certain aspects, the second therapeutic agent is an anti-inflammatory agent, a chemotherapeutic agent, a radiotherapeutic, an immunosuppressive agent, a cytotoxic drug, a targeted agent, a hormonal agent, or a support care agent.

Suitable anti-inflammatory agents include, but are not limited to, pentasa, mesalazine, asacol, codeine phosphate, benorylate, fenbufen, naprosyn, diclofenac, etodolac and indomethacin, aspirin and ibuprofen.

Suitable chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. Examples of suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC)), anti-mitotic agents, cis-dichlorodiamine platinum (II) (DDP) cisplatin), diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, E. coli L-asparaginase, emetine, epoetin-α, Erwinia L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

Suitable targeted agents include bevacizumab, sutinib, sorafenib, 2-methoxyestradiol or 2ME2, finasunate, PTK787, vandetanib, aflibercept, volociximab, etaracizumab (MEDI-522), cilengitide, erlotinib, cetuximab, panitumumab, gefitinib, trastuzumab, TKI258, CP-751,871, atacicept, rituximab, alemtuzumab, aldesleukine, atlizumab, tocilizumab, temsirolimus, everolimus, NPI-1387, MLNM3897, HCD122, SGN-40, HLL1, huN901-DM1, atiprimod, natalizumab, bortezomib, carfilzomib, NPI-0052, tanespimycin, saquinavir mesylate, ritonavir, nelfinavir mesylate, indinavir sulfate, belinostat, LBH589, mapatumumab, lexatumumab, AMG951, ABT-737, oblimersen, plitidepsin, SCIO-469, P276-00, enzastaurin, tipifarnib, perifosine, imatinib, dasatinib, lenalidomide, thalidomide, simvastatin, and celecoxib.

Suitable hormonal agents include anastrozole, letrozole, goserelin, tamoxifen, dexamethasone, prednisone, and prednisilone.

Suitable supportive care agents such as pamidronate, zoledonic acid, ibandronate, gallium nitrate, denosumab, darbepotin alpha, epoetin alpha, eltrombopag, and pegfilgrastim.

In certain aspects, the second therapeutic agent is any combination therapy regimen used for the treatment of non-Hodgkin's lymphomas. Typical regimens include:

| Regimen | Components | Duration |
|---|---|---|
| CHOP | CYCLOPHOSPHAMIDE [CTX] 750 mg/m2 IV ... D1 (D1 = day 1) | 21 days |
| | DOXORUBICIN [DOX] 50 mg/m2 IV ... D1 | |
| | VINCRISTINE [VCR] 1.4 mg/m2 IV ... D1 | |
| | PREDNISONE [Pred] 100 mg per day PO ... D1-5 | |
| CHOP-BLEO | CYCLOPHOSPHAMIDE [CTX] 750 mg/m2 IV ... D1 | 14 or 21 days |
| | DOXORUBICIN [DOX] 50 mg/m2 IV ... D1 | |
| | VINCRISTINE [VCR] 2 mg IV ... D1,5 | |
| | PREDNISONE [Pred] 100 mg per day PO ... D1-5 | |
| | BLEOMYCIN [BLEO] 15 units per day IV ... D1-5 | |
| CHOP-R | CYCLOPHOSPHAMIDE [CTX] 750 mg/m2 IV ... D1 (D1 = day 1) | 21 days |
| | DOXORUBICIN [DOX] 50 mg/m2 IV ... D1 | |
| | VINCRISTINE [VCR] 1.4 mg/m2 IV ... D1 | |
| | PREDNISONE [Pred] 100 mg per day PO ... D1-5 | |
| | RITUXAN IV ... D1 | |
| | (May be followed by 6-8 cycles of CHOP without Rituxan) | |
| COMLA | CYCLOPHOSPHAMIDE [CTX] 1500 mg/m2 IV ... D1 | 91 days |
| | VINCRISTINE [VCR] 1.4 mg/m2 IV ... D1,8,15 | |
| | METHOTREXATE [MTX] 120 mg/m2 IV ... | |
| | D22, 29, 36, 43, 50, 57, 64, 71 | |
| | LEUCOVORIN [Leu] 25 mg/m2 PO ... | |
| | D23, 30, 37, 44, 51, 58, 65, 72 | |
| | q6h × 4 doses beginning 24 hr post MTX | |
| | CYTARABINE [ARA-C] 300 mg/m2 IV ... | |
| | D22, 29, 36, 43, 50, 57, 64, 71 | |
| COP | CYCLOPHOSPHAMIDE [CTX] 400-800 mg/m2 IV ... D1 | 14 days |
| | VINCRISTINE [VCR] 2 mg IV ... D1 | |
| | PREDNISONE [Pred] 60 mg/m2 per day PO ... D1-5 | |
| | Followed by tapering dose 40, 20, 10 mg/day | |
| CVP-1 | CYCLOPHOSPHAMIDE [CTX] 400 mg/m2 per day PO ... D1-5 | 21 days |
| | VINCRISTINE [VCR] 1.4 mg/m2 IV ... D1 | |
| | PREDNISONE [Pred] 100 mg/m2 per day PO ... D1-5 | |
| DHAP | CISPLATIN [CDDP] 100 mg/m2 CIV over 24 hrs ... D1 | 3-4 weeks |
| | CYTARABINE [ARA-C] 2 g/m2 IV over 3 hrs ... D2 | |
| | After Cisplatin repeat dose 12 hrs later for total dose of 4 g/m2 | |
| | DEXAMETHASONE [DEX] 40 mg per day PO or IV ... D1-4 | |
| | For 4 days | |
| ESAP | METHYLPREDNISOLONE[SOL] 500 mg per day IV ... D1-4 | As tolerated |
| | ETOPOSIDE [VP-16] 40 mg/m2 per day IV ... D1-4 | |
| | CYTARABINE [ARA-C] 2 g/m2 IV ... D5 | |
| | Over 2 hr, after completion of Cisplatin | |
| | CISPLATIN [CDDP] 25 mg/m2 per day × 4 CIV ... D1-4 | |
| | (Total Dose 100 mg) | |

Other regimens are known in the art and can be used as "second therapeutic agents" in conjunction with an anti-CS1 antibody therapy. The chemotherapeutic regimens can be accompanied by anti-emetics, such as Compazine, Zofran or Kytril.

6. EXAMPLE 1

CS1 is Expressed in Nasal Type NK/T Cell Lymphomas and Angioimmunoblastic T-Cell Lymphomas Background:

CS1 (CRACC, SLAMF7, CD319) is a member of the signaling lymphocyte activating molecule-related receptor family. It is highly and uniformly expressed on the cell surface of benign and malignant plasma cells. Lower levels of CS1 have also been reported on NK cells and NK-like T-cells (NK/T). CS1 expression in NK and T-cell lymphomas—aggressive lymphomas for which no effective therapy exists—is unknown. The expression of CS1 in normal NK/T cells and in a series of NK and peripheral T-cell lymphomas (PTCL) was examined.

Methods:

CS1 expression in normal NK and T-cells were assessed by gene expression profiling using automated immunohistochemistry (IHC, Ventana Medical Systems). Flow cytometry (FACSCalibur, Becton Dickinson) was performed on blood from normal samples using a directly conjugated Alexa-488 elotuzumab (HuLuc63). Archival formalin-fixed, paraffin-embedded tissues from PTCLs, including angioimmunoblastic T-cell lymphomas (AITL) and nasal type NK/T cell lymphomas were tested for CS1 expression using the a paraffin-reactive 1G9 monoclonal antibody (described in Hsi et al., 2008, Clinical Cancer Research 14:2775-2784). The samples were then blocked with the Sniper reagent (Biocare) and the primary antibody applied at 2.5 µg/mL for 32 minutes at 37° C. Ventana DABmap with universal secondary antibody was used for antibody detection.

Result:

Gene expression profiling showed CS1 expression in purified NK and NK/T cells. Cell surface expression of CS1 protein on normal blood NK and NK/T cells (n=18 samples) was confirmed by flow cytometry with Alexa-488 HuLuc63. The majority of normal NK and NK/T cells expressed CS1 (mean % positive and standard deviation of 96%+/−4% and 71%+/−24%, respectively). Tumor samples from patients with nasal type NK/T cell lymphoma as well as other peripheral T-cell lymphomas by IHC were assayed for CS1 expression. Biopsies from 13 patients (5 from the United States, 8 from Korea) with nasal type NK/T cell lymphomas were evaluated by IHC. 12 of 13 (92%) patient samples expressed CS1 with most cases showing a majority of cells positive. 46 PTCLs were also evaluated (including 9 AITL). Overall, 8/46 (17%) of the PTCL cases expressed CS1. However, of the AITLs, 4 of 9 (44%) expressed CS1.

Conclusion:

CS1 is expressed on nearly all nasal type NK/T cell lymphomas and in a substantial proportion of AITLs.

7. EXAMPLE 2

CS1 is Expressed in Nasal Type NK/T Cell Lymphomas and Angioimmunoblastic T-Cell Lymphomas 7.1 Introduction CS1 (CD319, CRACC, SLAMF7) is a member of the signaling lymphocyte activating-molecule—related receptor family. It has recently been identified as a cell surface antibody target selectively expressed in plasma cells (Hsi et al., 2008, Clin. Cancer Res. 14:2775-2784). Other members of the signaling lymphocyte activating-molecule (SLAM)—related receptor family include SLAM (CD150), 2B4 (CD244), CD84, NTB-A (Ly-108), and Ly-9 (CD229). These molecules are characterized by two or four extracellular immunoglobulin (Ig)-like domains and an intracellular signaling domain with immune receptor tyrosine-based switch motifs with the consensus amino acid sequence TxYxxV/I.

A humanized antibody to CS1 (elotuzumab, also known as HuLuc63) is currently under investigation in relapsed multiple myeloma (Tai et al., 2008, Blood 112(4):1329-37; Tai et al., 2007, Blood. 110(5):1656-63). Although selectively expressed in benign and malignant plasma cells, CS1 is expressed at lower levels in normal NK cells and a subset of T-cells (Hsi et al., 2008, Clin. Cancer Res. 14:2775-2784). In this study, expression of CS1 in a series of T-cell lymphomas and nasal type NK cell, an aggressive lymphoma without satisfactory treatment options, was characterized.

7.2 Methods

Cases and Immunohistochemistry:

Study cases were derived from the archives of the Cleveland Clinic and Samsung Hospital. Diagnoses were established according to established criteria of the WHO classification for hematolymphoid tumors. For the mature T-cell lymphomas a tissue microarray was constructed using duplicate 1 mm diameter cores (Beecher Instruments). Immunohistochemistry was performed as described monoclonal antibodies to CD4 and CD8 (Ventana Medical Systems, Tucson Ariz.) or with the paraffin reactive anti-CS1 monoclonal antibody 1G9 (Hsi et al., 2008, Clin. Cancer Res. 14:2775-2784). Cases were considered positive if greater than 20% of tumor cells expressed CS1. HANK1 cells are an IL-2 dependent cell line derived from a nasal type NK/T lymphoma as previously described (Kagami et al., 1998, Br. J. Haematol. 103:669-677).

Flow Cytometry:

CS1 expression in normal NK and T-cells was assessed by gene expression profiling. Flow cytometry (FACSCalibur, Becton Dickinson) was performed on normal blood samples using a directly conjugated FITC-elotuzumab. Anti-CS1-PE mouse monoclonal antibodies (Clone 235614) for flow cytometry were obtained from R&D Systems (Minneapolis, Minn.).

7.3 Results 7.3.1 Peripheral Blood Lymphocyte (PBL) Flow Cytometry

Prior gene profiling studies have demonstrated CS1 expression in normal NK cells (Boles et al., 2001, Immunol Rev. 181:234-49; Boles et al., 2001, Immunogenetics. 52:302-307). Murine monoclonal antibodies to CS1 demonstrated high expression of CS1 in NK and NK/T cells (Hsi et al., 2008, Clin. Cancer Res. 14:2775-2784). Using directly conjugated elotuzumab, flow cytometry was performed in order to confirm expression patterns of CS1 in normal lymphocytes. 12 specimens were analyzed. B and CD4+ T-cells lacked appreciable amounts of CS1. However, NK cells and, to a lesser extent, CD16/56 positive-T-cells expressed CS1 (mean % positive and standard deviation of 97%+/−4% and 67%+/−29%, respectively) (FIG. 3). The expression of CS1 in peripheral T-cell lymphoma, not otherwise specified (PTCL NOS), angioimmunoblastic T-cell lymphoma (AITL), and nasal type NK/T cell lymphoma was evaluated. The results of this study are summarized in Table 2 below:

13 cases (92%) expressed CS1. Thus, as a group this lymphoma type more frequently expressed CS1 compared to the most common types of mature T-cell lymphomas (P<0.0001, Fisher exact). Examination of the nasal NK/T cell lymphoma cell line HANK1 by flow cytometry confirmed CS1 surface expression (FIG. 6).

7.4 Conclusions

The great majority of nasal type NK/T-cell lymphomas express CS1. CS1 is also expressed on certain PTCL NOS and AITL.

TABLE 2

CS1 expression in lymphocyte subsets

| CELL TYPE | PHENOTYPE | N | MEAN | SD |
|---|---|---|---|---|
| NK cells | % Elotuzumab+ of True NK (CD3−/CD(16+56)+) | 12 | 97 | 4 |
| NKT cells | % HuLuc63+ of CD3+/CD(16+56)+ | 12 | 67 | 29 |
| CD3+CD8+ | % Elotuzumab + of CD3+CD8+ | 12 | 51 | 20 |
| CD3+CD8+(16+56)+/− | % Elotuzumab + (CD16+56)+ of CD3+CD8+ | 12 | 17 | 13 |
| CD3+CD8+(16+56)+/− | % Elotuzumab + (CD16+56)− of CD3+CD8+ | 12 | 34 | 18 |
| CD4 cells | % Elotuzumab + of CD3+CD8− | 12 | 10 | 7 |
| B cells | % Elotuzumab + of CD20+HLA-DR+ | 12 | 4 | 7 |

7.3.2 CS1 Expression in T Cell Lymphoma and Nasal-Type NK/T Cell Lymphoma

A paraffin reactive CS1 antibody (clone 1 G9) was developed and used for immunohistochemistry in archival fixed tissues. FIG. 4 shows the pattern in normal tonsil in which scattered T-cells and plasma cells (enriched in subepithelial areas) are positive. 37 peripheral T-cell lymphomas consisting of 29 PTCL NOS from 27 patients and 8 AITLs were studied. 7/29 (24%) of PTCL NOS cases were positive. Two patients each had two biopsies. In one, both specimens were negative while in the other, one relapse specimen was negative while the initial specimen was positive. In the 6 CS1+ PTCL NOS specimens for which CD4 or CD8 expression could be assigned, 4 were CD8+. Only 1 of 8 (15%) AITLs were positive and this case was CD4+ (FIG. 5).

Because NK and NK-like T-cells expressed CS1, we also examined a series of nasal type NK/T cell lymphomas. 12 of All publications, patents, patent applications and other documents cited in this application are hereby incorporated by reference in their entireties for all purposes to the same extent as if each patient publication, patent, patent application or other document were patiently indicated to be incorporated by reference for all purposes.

While various specific embodiments have been illustrated and described, it will be appreciated that various changes can be made without departing from the spirit and scope of the invention(s).

What is claimed is:

1. A method of treating NK cell lymphoma comprising, administering to a human patient in need thereof a therapeutically effective amount of an anti-CS1 antibody or antigen binding fragment thereof, or an anti-CS1 antibody-drug conjugate comprising anti-CS1 antibody or antigen binding fragment conjugated to a cytotoxic agent.

2. The method of claim 1, wherein the anti-CS1 antibody or antigen binding fragment thereof, or the anti-CS1 antibody-drug conjugate, is administered as a monotherapy.

3. The method of claim 1, further comprising administering to said patient a second therapeutic agent.

4. The method of claim 1, wherein the anti-CS1 antibody or antigen binding fragment thereof, or the anti-CS1 antibody-drug conjugate, induces ADCC in cells of said lymphoma.

5. The method of claim 1, wherein the anti-CS1 antibody or antigen binding fragment thereof, or the anti-CS1 antibody-drug conjugate, comprises heavy chain CDR sequences of SEQ ID NOS:11, 12 and 13 and light chain CDR sequences of SEQ ID NOS:14, 15 and 16.

6. The method of claim 1, wherein the anti-CS1 antibody or antigen binding fragment thereof, or the anti-CS1 antibody-drug conjugate, comprises a heavy chain variable region of SEQ ID NO:9 and a light chain variable region of SEQ ID NO:10.

7. The method of claim 1, wherein the anti-CS1 antibody or antigen binding fragment thereof, or the anti-CS1 antibody-drug conjugate, competes with the monoclonal antibody Luc63, as produced by the hybridoma deposited with the American Type Culture Collection ("ATCC") and assigned accession no. PTA-5950, for binding to CS1.

8. The method of claim 1, wherein said NK cell lymphoma is positive for CS1 expression.

9. The method of claim 8, further comprising, prior to said administration, assaying said NK cell lymphoma for CS1 expression.

10. The method of claim 3, wherein the second therapeutic agent is a radiotherapeutic.

11. The method of claim 10, wherein the second therapeutic agent is a chemotherapeutic.

12. The method of claim 11 wherein the chemotherapeutic agent is a cytotoxic agent.

13. The method of claim 3, wherein the second therapeutic agent is an anti-angiogenic agent.

14. The method of claim 3, wherein the second therapeutic agent is a cytokine, a tyrosine kinase inhibitor, a kinase inhibitor, or an HDAC inhibitor.

15. The method of claim 3, wherein the second therapeutic agent is a combination therapy.

16. The method of claim 15, wherein the combination therapy is CHOP (Cyclophosphamide, Adriamycin, Vincristine, and Prednisone).

17. The method of claim 3, wherein the anti-CS1 antibody and the second therapeutic agent are administered simultaneously, sequentially or separately.

18. A method of treating NK cell lymphoma, NK/T cell lymphoma, angioimmunoblastic T-cell lymphoma (AITL), or peripheral T cell lymphoma not otherwise specified (PTCL-NOS), comprising, administering to a human patient in need thereof a therapeutically effective amount of an anti-CS1 antibody or antigen binding fragment thereof, or an anti-CS1 antibody-drug conjugate comprising an anti-CS1 antibody or antigen binding fragment conjugated to a cytotoxic agent, wherein the anti-CS1 antibody or antigen binding fragment thereof, or the anti-CS1 antibody-drug conjugate, competes with monoclonal antibody Luc63, as produced by the hybridoma deposited with the American Type Culture Collection ("ATCC") and assigned accession no. PTA-5950, for binding to CS1.

19. The method of claim 18, wherein the anti-CS1 antibody or antigen binding fragment thereof, or the anti-CS1 antibody-drug conjugate, is administered as a monotherapy.

20. The method of claim 18, further comprising administering to said patient a second therapeutic agent.

21. The method of claim 20, wherein the second therapeutic agent is a radiotherapeutic.

22. The method of claim 21, wherein the second therapeutic agent is a chemotherapeutic.

23. The method of claim 22, wherein the chemotherapeutic agent is a cytotoxic agent.

24. The method of claim 18, wherein the anti-CS1 antibody or antigen binding fragment thereof, or the anti-CS1 antibody-drug conjugate, induces ADCC in cells of said lymphoma.

25. The method of claim 18, wherein the anti-CS1 antibody or antigen binding fragment thereof, or the anti-CS1 antibody-drug conjugate, comprises heavy chain CDR sequences of SEQ ID NOS:11, 12 and 13 and light chain CDR sequences of SEQ ID NOS:14, 15 and 16.

26. The method of claim 18, wherein the anti-CS1 antibody or antigen binding fragment thereof, or the anti-CS1 antibody-drug conjugate, comprises a heavy chain variable region of SEQ ID NO:9 and a light chain variable region of SEQ ID NO:10.

27. A method of treating NK cell lymphoma, NK/T cell lymphoma, angioimmunoblastic T-cell lymphoma (AITL), or peripheral T cell lymphoma not otherwise specified (PTCL-NOS), comprising, administering to a human patient in need thereof a therapeutically effective amount of an anti-CS1 antibody or antigen binding fragment thereof, or an anti-CS1 antibody-drug conjugate comprising anti-CS1 antibody or antigen binding fragment conjugated to a cytotoxic agent, wherein the anti-CS1 antibody or antigen binding fragment thereof, or the anti-CS1 antibody-drug conjugate, competes with the monoclonal antibody Luc90, as produced by the hybridoma deposited with the ATCC and assigned accession no. PTA-5091, for binding to CS1.

28. The method of claim 27, wherein the anti-CS1 antibody or antigen binding fragment thereof, or the anti-CS1 antibody-drug conjugate, is administered as a monotherapy.

29. The method of claim 27, further comprising administering to said patient a second therapeutic agent.

30. The method of claim 29, wherein the anti-CS1 antibody or antigen binding fragment thereof, or the anti-CS1 antibody-drug conjugate, induces ADCC in cells of said lymphoma.

* * * * *